United States Patent
Kitagawa

(10) Patent No.: US 7,931,861 B2
(45) Date of Patent: Apr. 26, 2011

(54) SAMPLE ANALYZER

(75) Inventor: Nobuhiro Kitagawa, Akashi (JP)

(73) Assignee: Sysmex Corporation, Hyogo (JP)

( * ) Notice: Subject to any disclaimer, the term of this patent is extended or adjusted under 35 U.S.C. 154(b) by 1003 days.

(21) Appl. No.: 11/803,778

(22) Filed: May 16, 2007

(65) Prior Publication Data

US 2007/0269342 A1  Nov. 22, 2007

(30) Foreign Application Priority Data

May 18, 2006 (JP) .................................. 2006-139319

(51) Int. Cl.
 G01N 21/00 (2006.01)
 G01N 31/00 (2006.01)
 G01N 33/00 (2006.01)
 B65G 47/12 (2006.01)
 B65G 43/00 (2006.01)

(52) U.S. Cl. ............. 422/63; 422/65; 198/443; 198/444

(58) Field of Classification Search .................... None
 See application file for complete search history.

(56) References Cited

U.S. PATENT DOCUMENTS

| | | | |
|---|---|---|---|
| 3,086,639 A | | 4/1963 | Donofrio |
| 5,065,852 A | * | 11/1991 | Marti .............................. 198/392 |
| 5,582,796 A | * | 12/1996 | Carey et al. ...................... 422/65 |
| 6,325,129 B1 | * | 12/2001 | Wright et al. ................... 156/538 |
| 6,790,412 B2 | | 9/2004 | Willenbring et al. |
| 2002/0106305 A1 | * | 8/2002 | Willenbring et al. ............ 422/63 |
| 2004/0109791 A1 | | 6/2004 | Itoh |
| 2007/0148042 A1 | * | 6/2007 | Ootani et al. .................... 422/63 |
| 2007/0212260 A1 | * | 9/2007 | Fukuda et al. ................... 422/64 |

FOREIGN PATENT DOCUMENTS

| | | |
|---|---|---|
| CA | 2254017 A1 | 5/2000 |
| GB | 1431968 | 4/1976 |
| JP | 2000019182 A * | 1/2000 |
| WO | WO 99/28724 | 6/1999 |

OTHER PUBLICATIONS

European Search Report for Application No. EP 07009690 dated Dec. 10, 2007.

* cited by examiner

*Primary Examiner* — Jill Warden
*Assistant Examiner* — Charles Hammond
(74) *Attorney, Agent, or Firm* — Brinks Hofer Gilson & Lione

(57) ABSTRACT

The present invention is to present a sample analyzer which can conduct a stable feeding of container used for preparing a measuring sample. The sample analyzer comprises: a first storage section for storing a plurality of containers, the container used for preparing a measurement sample; a first transport section for transporting the containers stored in the first storage section; a second storage section for storing the containers transported by the first transport section; a second transport section for transporting one by one the containers stored in the second storage section; a detector for detecting a state of transporting containers by the second transport section; a controller for controlling an operation of the first transport section based on a detection result of the detector; a sample preparing section for preparing a measurement sample in the container transported by the second transport section; and an analyzing section for analyzing the measurement sample prepared by the sample preparing section.

18 Claims, 19 Drawing Sheets

SAMPLE ANALYZER

RELATED APPLICATIONS

This application claims priority under 35 U.S.C. §119 to Japanese Patent Application No. 2006-139319 filed May 18, 2006, the entire content of which is hereby incorporated by reference.

FIELD OF THE INVENTION

The present invention relates to a sample analyzer, specifically relates to a sample analyzer which comprises a storage section for storing containers used for preparing measurement samples.

BACKGROUND

An example of a conventional automated chemical analyzer (sample analyzer) provided with a storage section for storing cuvettes (containers for preparing measurement samples) is disclosed in U.S. Pat. No. 6,790,412.

The automated chemical analyzer disclosed in U.S. Pat. No. 6,790,412 is provided with a vessel hopper for storing cuvettes, a rotatable elevator chain on the perimeter of which are mounted a plurality of protruding scoopers disposed at equal intervals, escrow guide, and first ram and second ram for feeding cuvettes to the escrow guide. In U.S. Pat. No. 6,790,412, cuvettes positioned at the bottom among the plurality of cuvettes stored in the vessel hopper are held one by one by the scoopers oriented in a predetermined direction. The cuvettes held by the scoopers are conveyed upward from the bottom of the vessel hopper by the elevator chain. Then, the cuvettes conveyed upward are dropped into the escrow guide from above by the first ram or second ram. Next, the cuvettes are transported one by one from the escrow guide.

High speed automated analyzers have been developed in recent years. For this reason, there is increasing desire for the capability of storing as many cuvettes as possible in the vessel hopper in order to reduce the number of times an operator must resupply cuvettes when continuously measuring a large number of samples.

In U.S. Pat. No. 6,790,412, however, cuvettes accommodated at the bottom of the vessel hopper are unregulatedly disoriented and sequentially taken out and moved upwardly by the many scoopers provided on the elevator chain, which face in a predetermined direction. In the art disclosed in U.S. Pat. No. 6,790,412, when the amount of cuvettes stored in the vessel hopper is increased in response to the previously mentioned demand for higher capacity, the unregulatedly disoriented cuvettes accommodated at the bottom of the vessel can not move freely. For this reason, it becomes difficult for each scooper to reliably take out a cuvette. Thus, a problem arises in the art disclosed in U.S. Pat. No. 6,790,412 in that it is difficult to conduct the stable feeding of cuvettes.

SUMMARY OF THE INVENTION

A first aspect of the present invention is a sample analyzer comprising: a first storage section for storing a plurality of containers, the container used for preparing a measurement sample; a first transport section for transporting the containers stored in the first storage section; a second storage section for storing the containers transported by the first transport section; a second transport section for transporting one by one the containers stored in the second storage section; a detector for detecting a state of transporting containers by the second transport section; a controller for controlling an operation of the first transport section based on a detection result of the detector; a sample preparing section for preparing a measurement sample in the container transported by the second transport section; and an analyzing section for analyzing the measurement sample prepared by the sample preparing section.

A second aspect of the present invention is a sample analyzer comprising: a first storage section for storing a plurality of containers, the container used for preparing a measurement sample; a first transport section for transporting the containers stored in the first storage section; a second storage section for storing the containers transported by the first transport section; a second transport section for transporting one by one the containers stored in the second storage section; a detector for detecting the amount of containers stored in the second storage section; a controller for controlling an operation of the first transport section based on a detection result of the detector; a sample preparing section for preparing a measurement sample in the container transported by the second transport section; and an analyzing section for analyzing the measurement sample prepared by the sample preparing section.

A third aspect of the present invention is a sample analyzer comprising: a first storage section for storing a plurality of containers, the container used for preparing a measurement sample; a first transport section for transporting the containers stored in the first storage section; a second storage section for storing the containers transported by the first transport section; a second transport section for transporting one by one the containers stored in the second storage section; a detector for detecting the amount of containers transported by the second transport section from the second storage section; a controller for controlling an operation of the first transport section based on a detection result of the detector; a sample preparing section for preparing a measurement sample in the container transported by the second transport section; and an analyzing section for analyzing the measurement sample prepared by the sample preparing section.

DETAILED DESCRIPTION OF THE PREFERRED EMBODIMENTS

The embodiment of the present invention is described hereinafter based on the drawings.

The structure of the embodiment of the sample analyzer 1 of the present invention is first described with reference to FIGS. 1 through 18.

The embodiment of the sample analyzer 1 of the present invention optically measures and analyzes the amount and degree of activity of specific substances related to coagulation and fibrinolytic functions of the blood using blood plasma as a sample. The sample analyzer 1 of the present embodiment optically measures a sample using a coagulation time method, synthetic substrate method and immunoturbidity method (main measurement). The coagulation method used in the present embodiment detects and measures the change of transmission light while a sample coagulates. Measurement items include PT (prothrombin time), APTT (active partial thromboplastin time), and Fbg (fibrinogen content) and the like. Measurement items of the synthetic substrate method include ATIII and the like, and those of the immunoturbidity method include D-dimer, FDP and the like.

Figure 1:
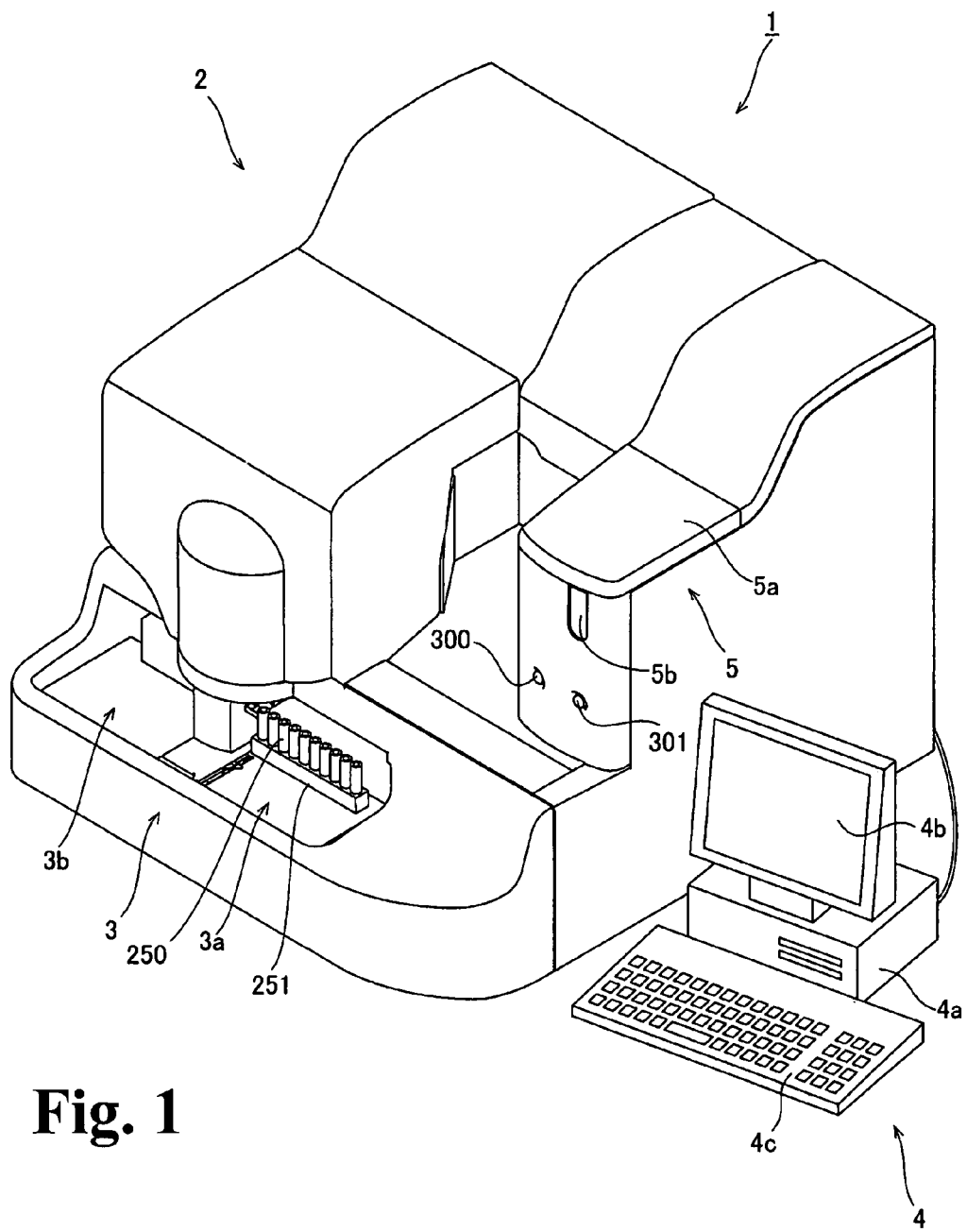
FIG. 1 is a perspective view of the exterior of an embodiment of the sample analyzer of the present invention.
Figure 2:
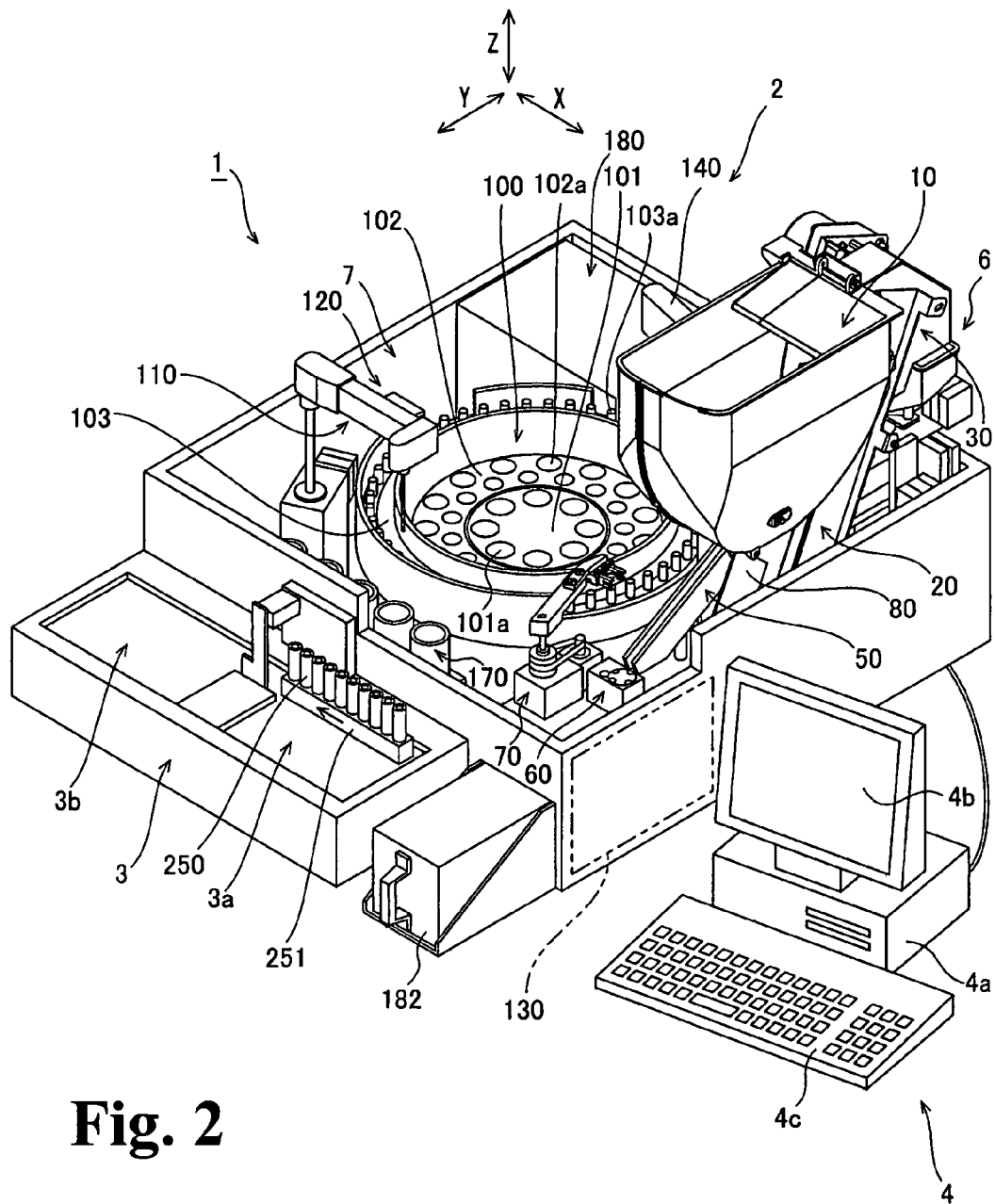
FIG. 2 is a perspective view of the general structure of an embodiment of the sample analyzer of the present invention.

As shown in FIGS. 1 and 2, the sample analyzer 1 includes a detection section 2, transport section 3 disposed to the front side of the detection section 2, and a control device 4 electrically connected to the detection section 2. The detector 2 is provided with a cuvette receiver 5 into which is supplied a cuvette 200 for containing a sample to be measured. The cuvette receiver 5 is provided with an openable cover 5a, and a window 5b through which the interior of the cuvette receiver 5 is viewable. The front side of the cuvette receiver 5 is provided with an emergency stop button 300, and measurement start button 301. The cover 5a (refer to FIG. 1) is provided to allow a cuvette 200 to be supplied into the first storage section 10 (refer to FIG. 2) of the cuvette feeder 6, which is described later. The user can see the remaining amount of cuvettes 200 stored in the first storage section 10 through the window 5b (refer to FIG. 2). The emergency stop button 300 (FIG. 1) functions to stop a measurement in case of necessity. The measurement start button 301 (FIG. 1) is configured to start a measurement when pressed. Thus, a user can immediately start a measurement operation after supplying a cuvette 200. Measurement may also be started by an operation of the control device 4.

The control device 4 is a personal computer 401 (PC), and includes a controller 4a, display 4b, and keyboard 4c, as shown in FIGS. 1 and 2. The controller 4a controls the operations of both the detection section 2 and transport section 3, and functions to analyze the optical information of a sample obtained by the detection device 2. The controller 4a is configured by a CPU, ROM, RAM and the like. The display 4b is provided to display information relating to interference substances (hemoglobin, chyle (lipids), and bilirubin) present in the sample, and display the analysis results obtained by the controller 4a.

Figure 4:
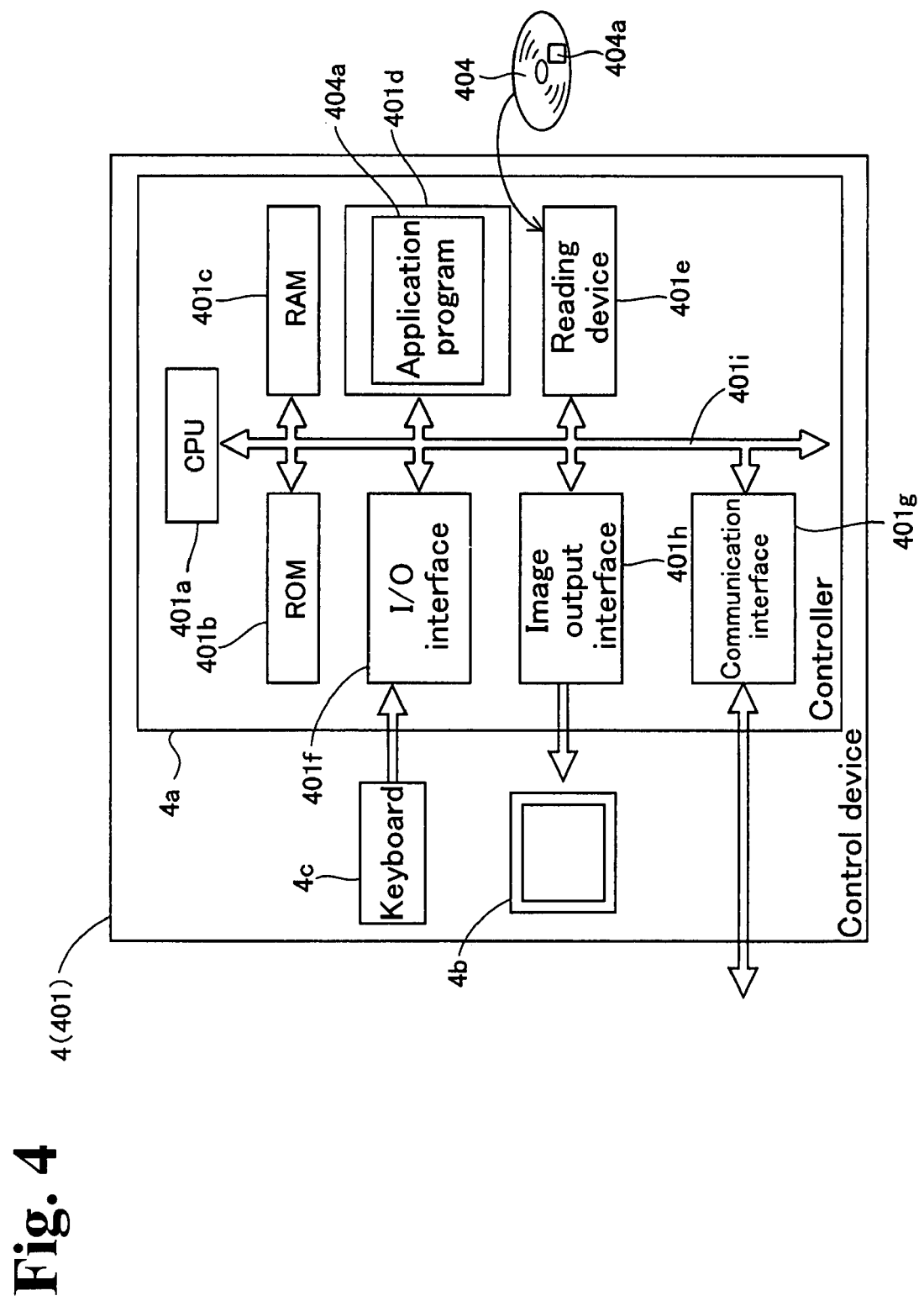
FIG. 4 is a block diagram of the control device of the sample analyzer shown in FIG. 2.

The construction of the control device 4 is described below. As shown in FIG. 4, the controller 4a is mainly configured by a CPU 401a, ROM 401b, RAM 401c, hard disk 401d, reading device 401e, I/O interface 401f, communication interface 401g, and image output interface 401h. The CPU 401a, ROM 401b, RAM 401c, hard disk 401d, reading device 401e, I/O interface 401f, communication interface 401g, and image output interface 401h are connected by a bus 401i.

The CPU 401a is capable of executing computer programs stored in the ROM 401b, and computer programs loaded in the RAM 401c. The computer 401 functions as the control device 4 when the CPU 401a executes an application program 404a described later.

The ROM 401b is configured by a mask ROM, PROM, EPROM, EEPROM or the like, and stores computer programs executed by the CPU 401a and data and the like used in conjunction therewith.

The RAM 401c is configured by SRAM, DRAM or the like. The RAM 401c is used when reading the computer program recorded in the ROM 401b and on the hard drive 401d. The RAM 401c is further used as a work area of the CPU 401a when these computer programs are being executed.

The hard drive 401d contains various installed computer programs to be executed by the CPU 401a such as an operating system and application programs and the like, and data used in the execution of these computer programs. Also installed on the hard disk 401d is the application program 404a used to calculate the presence and concentration of interference substances in the present embodiment.

The reading device 401e is configured by a floppy disk drive, CD-ROM drive, DVD-ROM drive or the like, and is capable of reading the computer programs and data stored on a portable recording medium 404. Furthermore, the portable recording medium 404 may also store the application program 404a in the present embodiment; the computer 401 is capable of reading the application program 404a from the portable recording medium 404 and installing the application program 404a on the hard disk 401d.

Not only may the application program 404a be provided by the portable recording medium 404, it also may be provided from an external device connected to the computer 401 so as to be capable of communication over an electric communication line by means of the electric communication line (wire line or wireless). For example, the application program 404a may be stored on the hard disk of a server computer connected to the internet, such that the computer 401a can access the server computer and download the application program 404a, and then install the application program 404a on the hard disk 401d.

Also installed on the hard disk 401d is an operating system providing a graphical user interface, such as, for example, Windows (registered trademark) of Microsoft Corporation, U.S.A. In the following description, the application program 404a of the present embodiment operates on such an operating system.

The I/O interface 401f is configured by a serial interface such as a USB, IEEE1394, RS232C or the like, parallel interface such as SCSI, IDE, IEEE1284 or the like, analog interface such as a D/A converter, A/D converter or the like. The keyboard 4c is connected to the I/O interface 401f, such that a user can input data in the computer 401 using the keyboard 4c.

The communication interface 401g is Ethernet (registered trademark) interface, for example. The computer 401 can send and receive data to and from the detection device 2 using a predetermined communication protocol via the communication interface 401g.

The image output interface 401h is connected to the display 4b configured by an LCD, CRT or the like, such that image signals corresponding to the image data received from the CPU 401a can be output to the display 4b. The display 4b displays an image (screen) in accordance with the input image signals.

Figure 3:
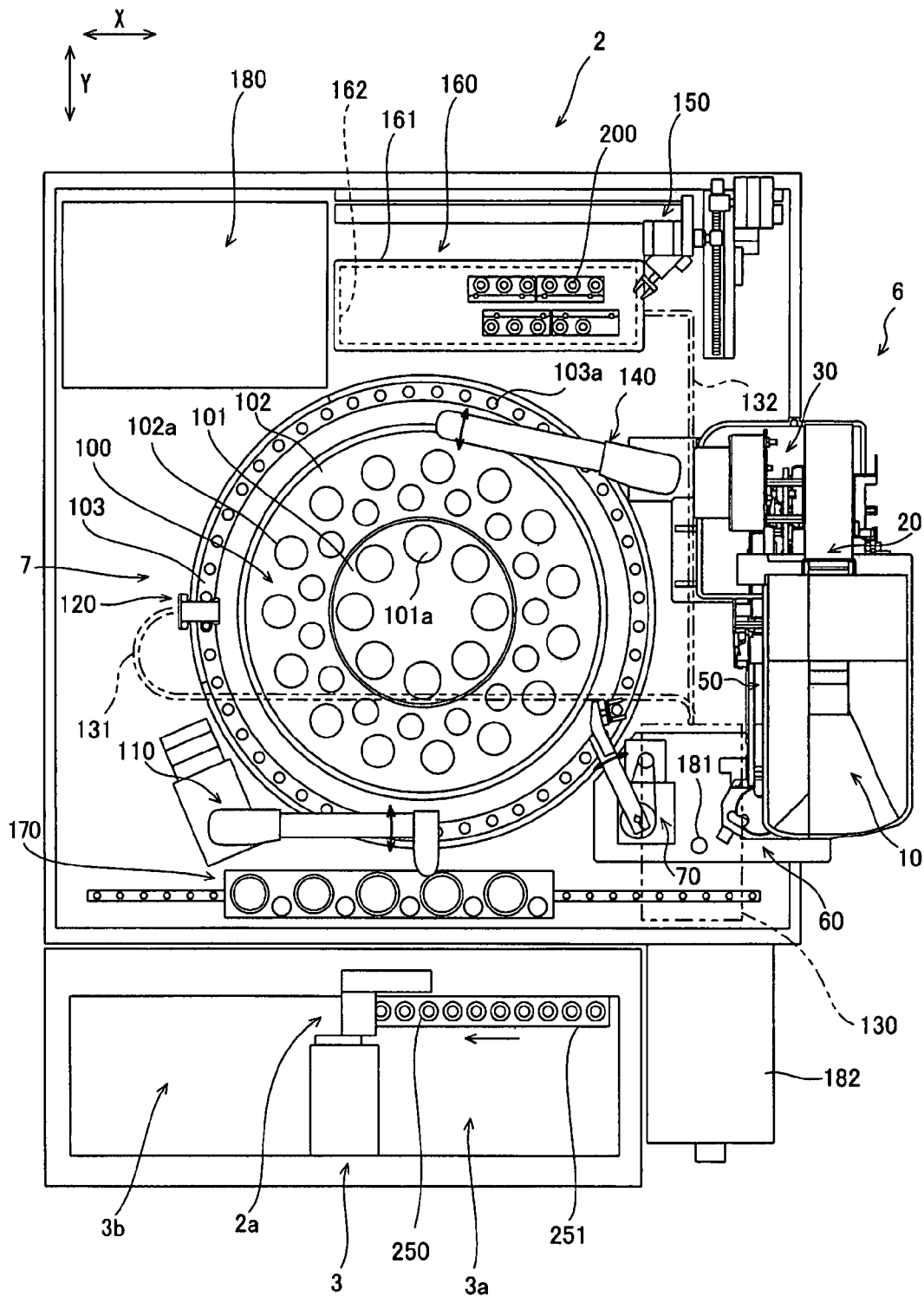
FIG. 3 is a top view showing the sample analyzer shown in FIG. 2 with the control device removed.

As shown in FIGS. 1 through 3, the transport device 3 functions to transport a rack 251 containing a plurality of test tubes 250 (ten in the present embodiment) that contain samples to the aspirating position 2a of the detection section 2 (refer to FIG. 2) in order to supply samples to the detection section 2. Furthermore, the transport device 3 has a rack set region 3a that accommodates the racks 251 that hold the test tubes 250 containing unprocessed samples, and a rack receiving region 3b that accommodates the racks 251 that hold test tubes 250 containing processed samples.

The detection device 2 is configured to obtain optical information relating to a supplied sample by optically measuring a sample supplied from the transport device 3. In the present embodiment, optical measurement is performed on a sample dispensed into a cuvette 200 (refer to FIG. 3) in the detection section 2 from a test tube 250 loaded in the rack 251 in the transport device 3.

Figure 5:
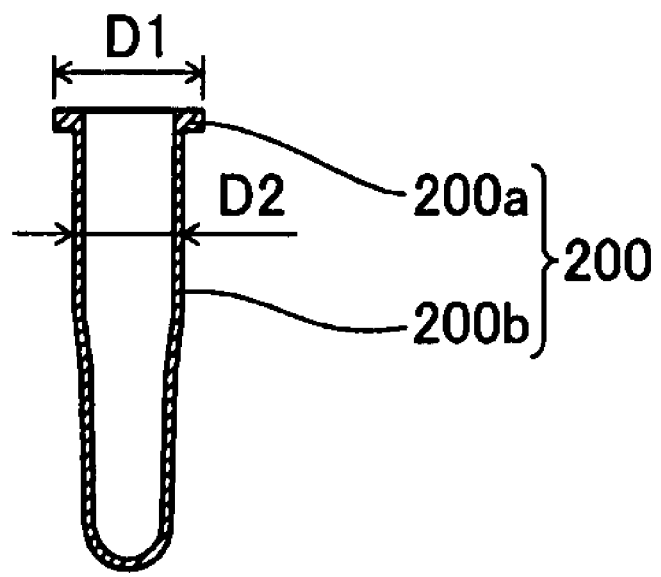
FIG. 5 is a cross section view of a cuvette used in the embodiment of the sample analyzer of the present invention.

The detection section 2 includes a cuvette feeder 6 and analyzing section 7. The cuvette feeder 6 is provided to supply one by one the plurality of cuvettes 200 (refer to FIG. 5) directly supplied by a user to the rotating part 100 of the analyzing section 7. As shown in FIG. 5, the cuvette 200 is configured by a flange 200a having a diameter D1 (approximately 10 mm), and body 152b having a diameter D2 (approximately 8 mm) which is smaller than the diameter D1. The cuvette 200 is approximately 30 mm in length.

As shown in FIGS. 6 through 9, the cuvette feeder 6 of the present embodiment includes a first storage section 10 into which cuvettes 200 are supplied, cuvette transport section 20 for transporting the cuvette 200 from the first storage section 10, second storage section 30 for storing the cuvette 200 transported from the first storage section 10 by the cuvette transport section 20, cuvette take-out section 40 for taking out one at a time the cuvette 200 from the second storage section 30, moving section 50 provided with an inclination for moving the cuvette 200 taken out by the cuvette take-out section 40, rotating part 60 disposed at the bottom end of the moving part 50, catchers 70 provided at predetermined intervals from the rotating part 60, and brackets 80 for supporting the first storage section 10, cuvette transport section 20, second storage section 30, and cuvette take-out section 40.

The first storage section 10 includes a first hopper 11 for storing cuvettes 200, sensor 12 mounted below the bottom surface of the first hopper 11, and movable panel 13 mounted adjacent to the bottom part of the first hopper 11. The first hopper 11 is formed of semitransparent resin to allow the amount of cuvettes 200 stored in the first hopper 11 to be viewed by a user through the previously mentioned window 5b (refer to FIG. 1). The lower part of the hopper 11 is provided with an opening 11a through which passes the holding panel 21a of the endless belt 21 described later. The cuvette storage area 21b (refer to FIG. 9) formed by the first hopper 11 and endless belt 21 is sufficiently large to accommodate approximately 1,000 cuvettes 200. The sensor 12 is a transmission type sensor that functions to detect that the amount of cuvettes 200 stored in the first hopper 11 is less than 100 cuvettes. The sample analyzer 1 is configured so as to warn the user when the sensor 12 has detected that the amount of remaining cuvettes 200 is low via a warning sound or the like. The movable panel 13 is mounted on a rotating shaft 13a of the first hopper 11 so as to be rotatable. The movable panel 13a is mounted so as to cover the opening 11a. The bottom surface at the end of the movable panel 13 on the opposite side from the rotating shaft 13a is configured so as to contact a surface 21b (refer to FIGS. 9 and 10) of the holding panel 21a provided on the endless belt 21. The movable panel 13 prevents the cuvette 200 from dropping downward through the opening 11a of the first hopper 11 without impeding the operation of the endless belt 21.

Figure 9:
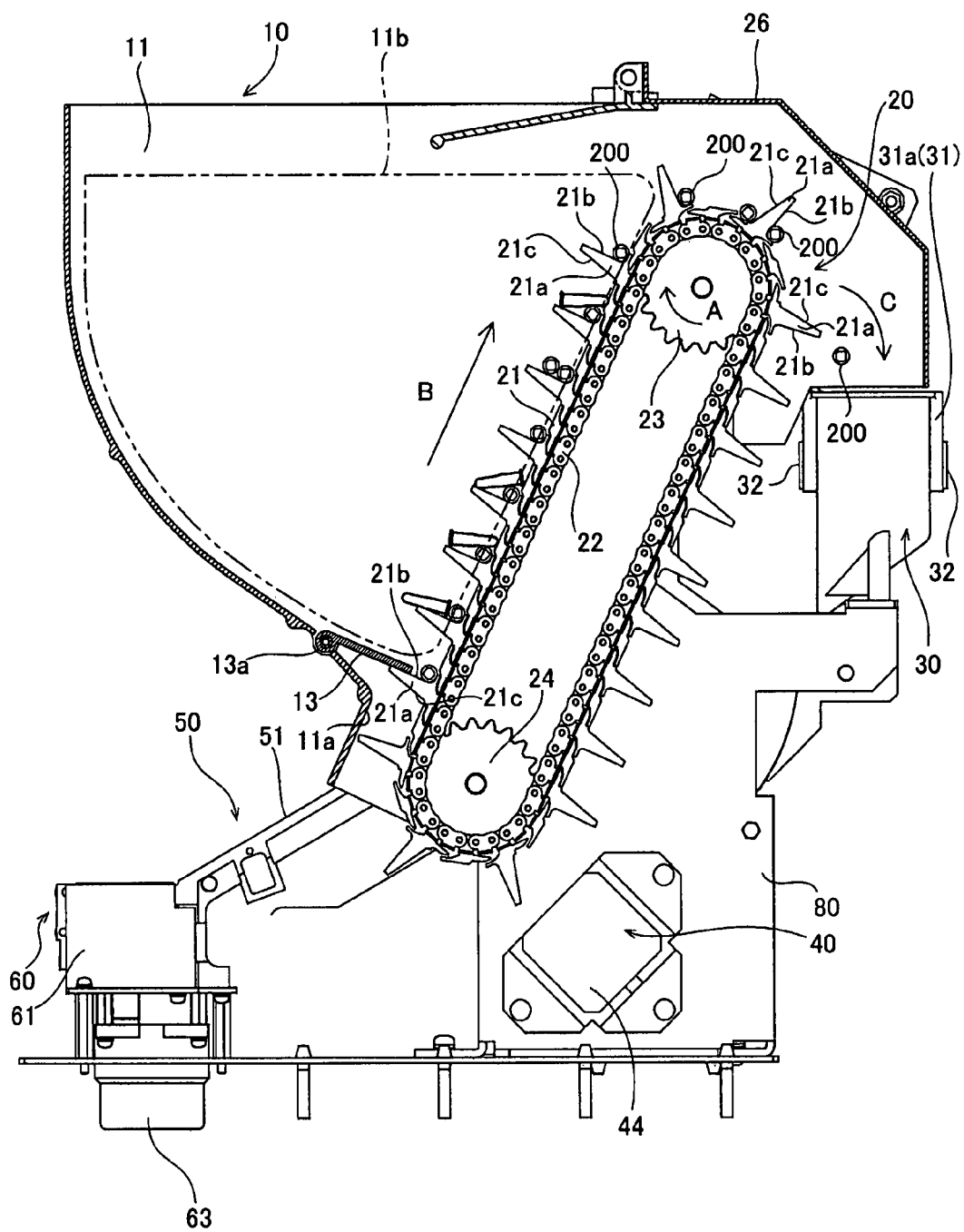
FIG. 9 is a cross section view showing details of the first hopper of FIG. 7.
Figure 10:
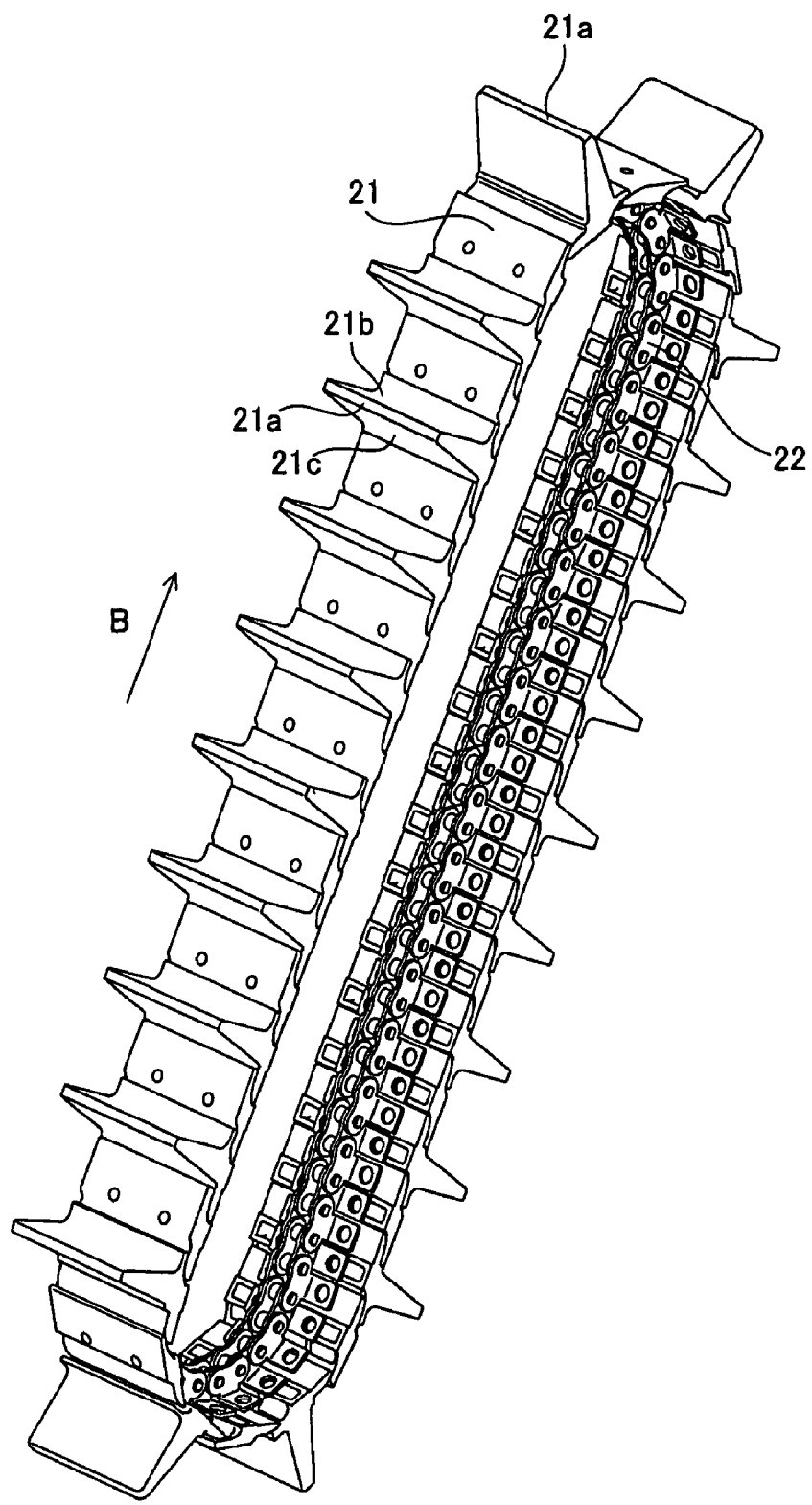
FIG. 10 is a perspective view of the endless belt and chain of the cuvette transport section of an embodiment of the sample analyzer of the present invention.
Figure 11:
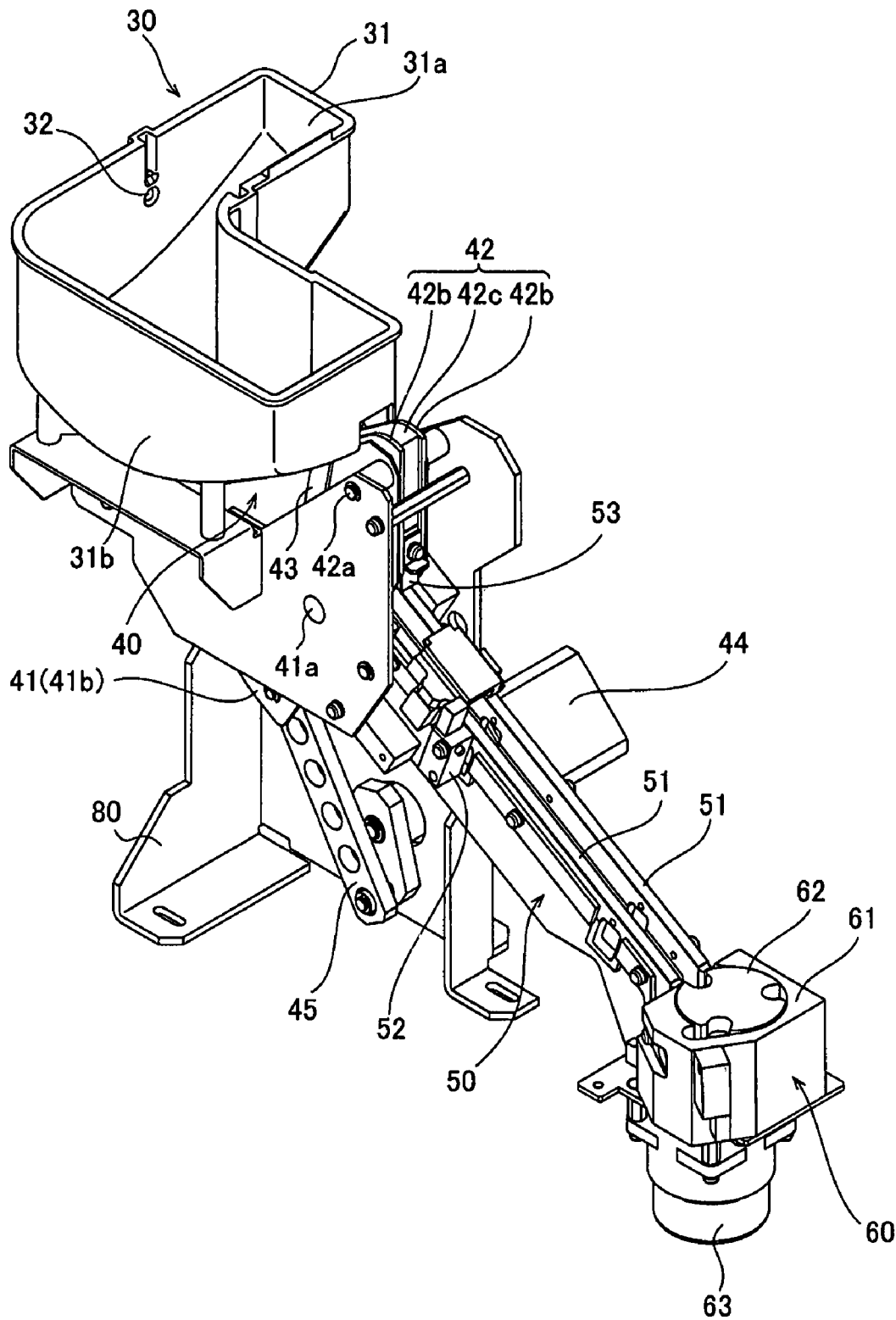
FIG. 11 is a perspective view showing the cuvette feeder device shown in FIG. 6 with the first storage section and cuvette transport section removed.
Figure 12:
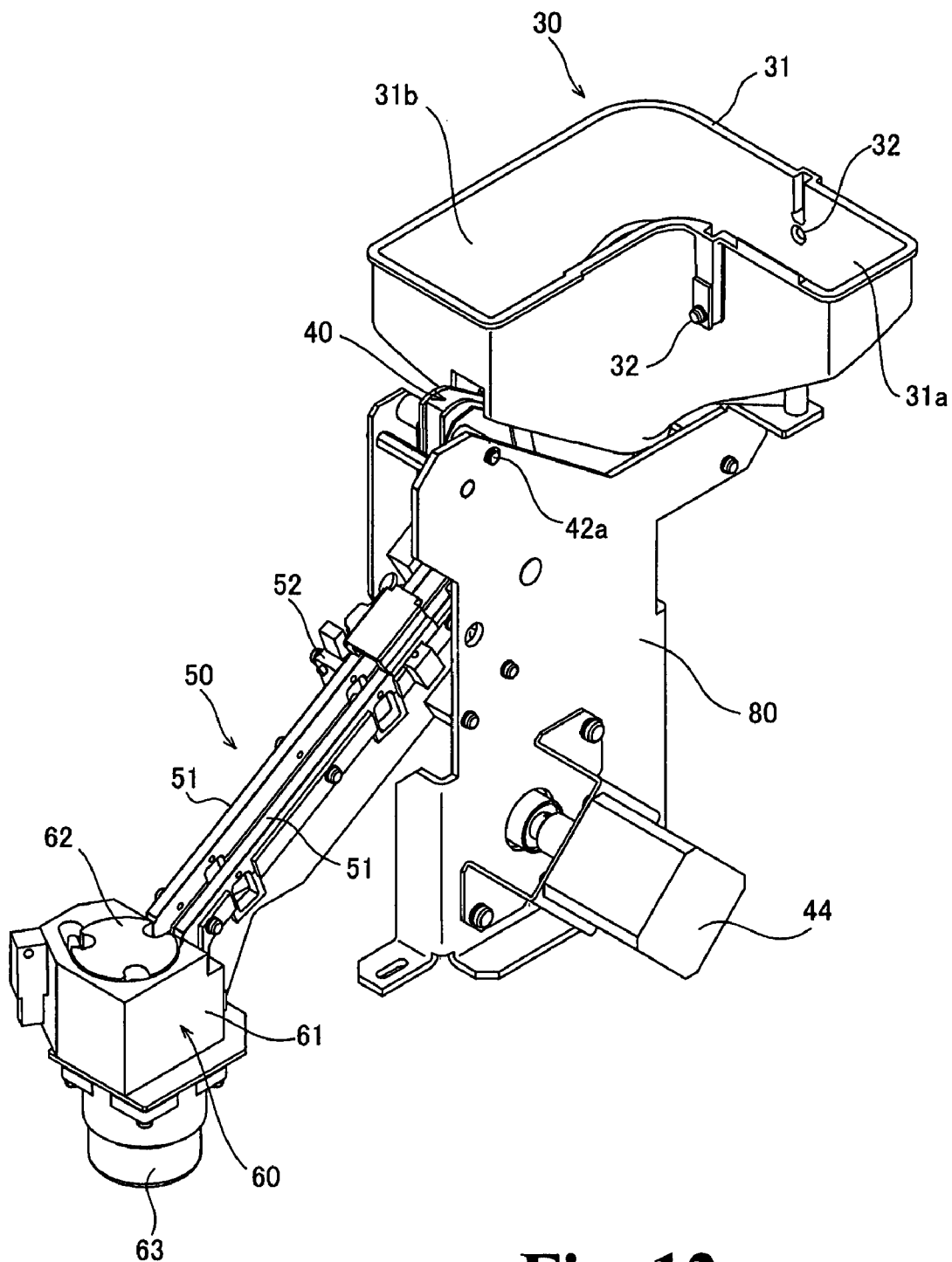
FIG. 12 is a perspective view looking at FIG. 11 from another direction.

The cuvette transport section 20 includes an endless belt 21 provided with a plurality of holding panels 21a, chain 22 on which the endless belt is mounted, sprocket 23 and sprocket 24 that engage the chain 22, drive motor 25 for driving the sprocket 23, and cover 26 for housing the endless belt 21. As shown in FIG. 9, the endless belt 21 is rotated in the arrow B direction via the rotation of the sprocket 23 in the arrow A direction by the drive motor 25. The plurality of holding panels 21a are approximately 32 mm in width and 15 mm in length, and each holding panel 21a has a size capable of holding one to three individual cuvettes 200 which have a diameter of approximately 10 mm and length of 30 mm. That is, the endless belt 21 functions to transport the cuvettes 200 stored in the first hopper from the bottom part of the first hopper 11 in an upward direction. As shown in FIG. 9, the orientation of the cuvette 200 is not necessarily uniform when the cuvettes 200 are held by the holding panels 21a of the endless belt 21 in the present embodiment. The sprockets 23 and 24 are disposed such that the endless belt 21 is inclined at a predetermined angle relative to the perpendicular direction on the second storage section 30 side. Thus, the cuvettes 200 are prevented from falling from the holding panels 21a when the endless belt 21 transports the cuvettes 200 upward from the bottom part of the first hopper 11.

The cuvettes 200 which are lifted while held by the holding panels 21a of the endless belt 21 drop to the opposite side of the first hopper 11 (arrow C direction in FIG. 9) in conjunction with the rotation of the endless belt 21. Since the second storage section 30 is disposed so as to be the destination of the dropping cuvettes 200, the cuvettes 200 which are transported from the first hopper 11 are stored in the second storage section 30. The surface 21b on the side of the holding panel 21a in the arrow B direction is provided to be nearly perpendicular to the surface of the endless belt 21, whereas the surface 21c of the holding panel 21a on the side opposite to the B direction is provided so as to be inclined at a predetermined angle in the clockwise direction from the perpendicular relative to the surface of the endless belt 21. Thus, the cuvette 200 readily drops into the second storage section 30 when the holding panels 21a are reached the vicinity of the second storage section 30.

The second storage section 30 includes a second hopper 31 and transmission type sensor 32, as shown in FIGS. 11 through 14. The second hopper 31 is L-shaped when viewed planarly, and includes a cuvette receiver 31a and cuvette stacker 31b. A cuvette 200 which has dropped from the endless belt 21 is delivered to the cuvette receiver 31a of the second hopper 31. The inside bottom surface of the second hopper 31 inclines downward from the cuvette receiver 31a toward the cuvette stacker 31b, such that a cuvette 200 delivered to the cuvette receiver 31a is automatically moved to the cuvette stacker 31b. The second hopper 31 has a cuvette storage capacity (approximately 100 cuvettes 200) that is less than the storage capacity of the first hopper (approximately 1,000 cuvettes 200). When the cuvettes 200 stored in the second hopper 31 exceed a predetermined amount, their presence is detected by a sensor 32. In the present embodiment, the second hopper 31 is determined to be full when the sensor 32 detects the presence of the cuvettes 200, and the operation of the endless belt 21 is stopped by stopping the operation of the drive motor 25. An oscillating rail 41 and oscillating guide 42 of the cuvette take-out section 40 are disposed at the opening 31c (refer to FIG. 13) provided at the bottom part of the cuvette stacker 31b of the second hopper 31.

Figure 15:
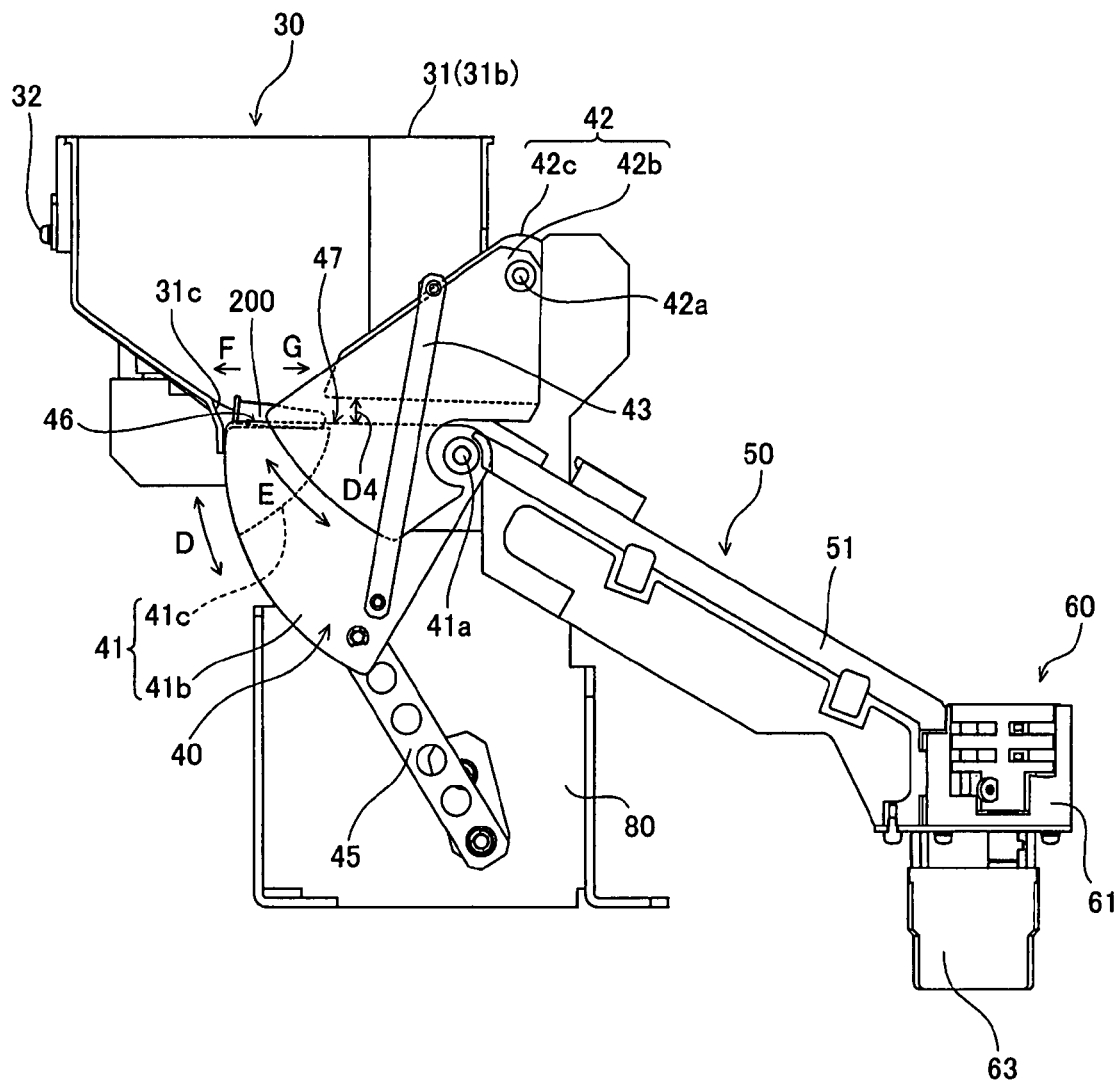
FIG. 15 is a cross section view of the cuvette take-out section shown in FIG. 12.
Figure 16:
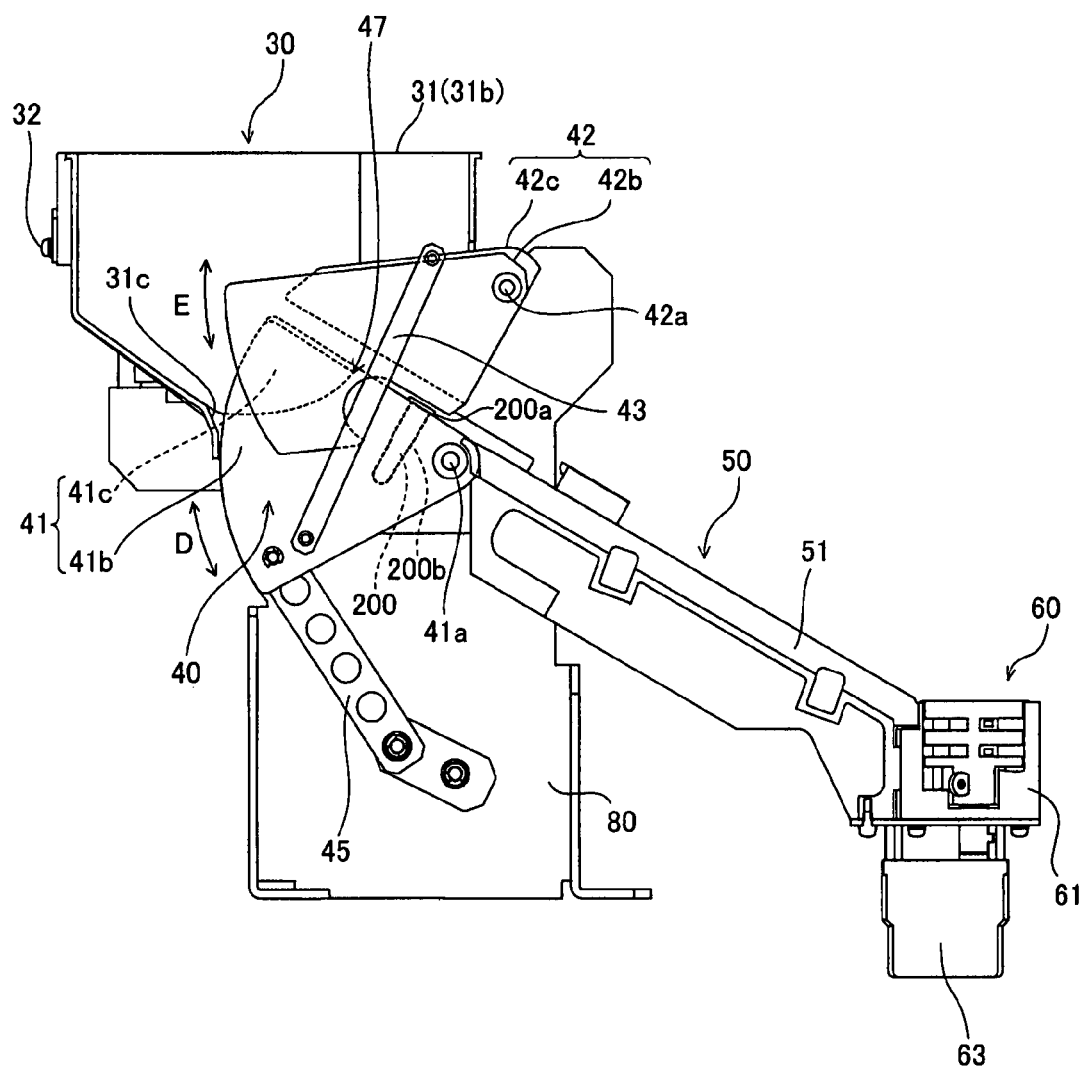
FIG. 16 is a cross section view showing the fan shaped plate of the cuvette take-out section of FIG. 14 disposed at the top dead center.

The cuvette take-out section 40 includes the oscillating rail 41 which is rotatable around the rotating shaft 41a, oscillating guide 42 which is rotatable around the rotating shaft 42a, link 43 which integratedly links the oscillating rail 41 and oscillating guide 42 so as to be rotatable, drive motor 44, and arm 45 for transmitting the drive force of the drive motor 44, as shown in FIGS. 11 through 16. When the drive motor 44 is actuated, the oscillating rail 41 is oscillated by the arm 45 which is rotated by the drive motor 44. Since the oscillating rail 41 is linked to the oscillating guide 42, the oscillating guide 42 is oscillated in conjunction with the oscillation of the oscillating rail 41. As shown in FIGS. 15 and 16, the oscillating rail 41 and oscillating guide 42 respectively oscillate in the D direction and E direction around the rotating shafts 41a and 42a.

Figure 13:
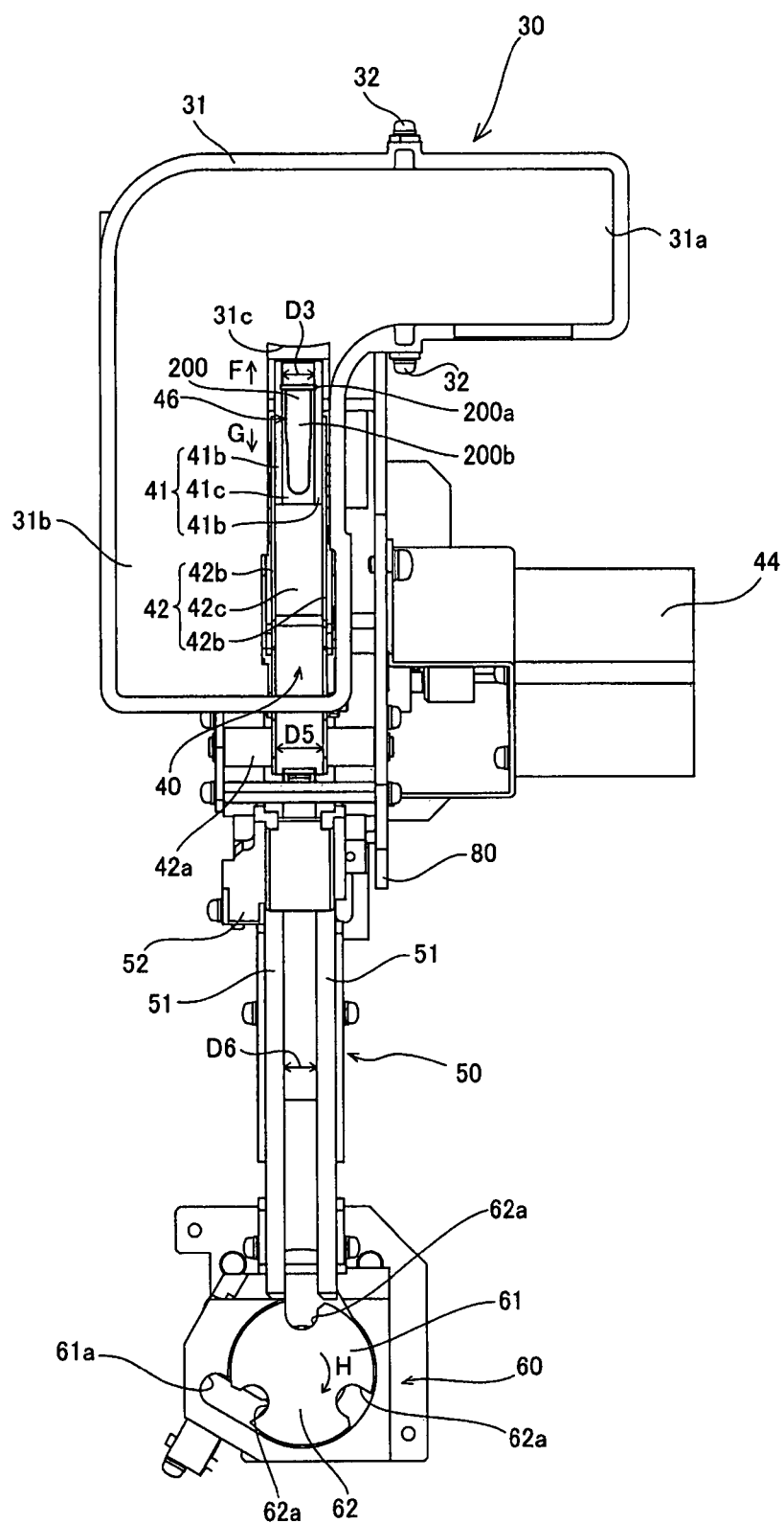
FIG. 13 is a top view showing the condition that a cuvette is disposed at the take-out position.
Figure 14:
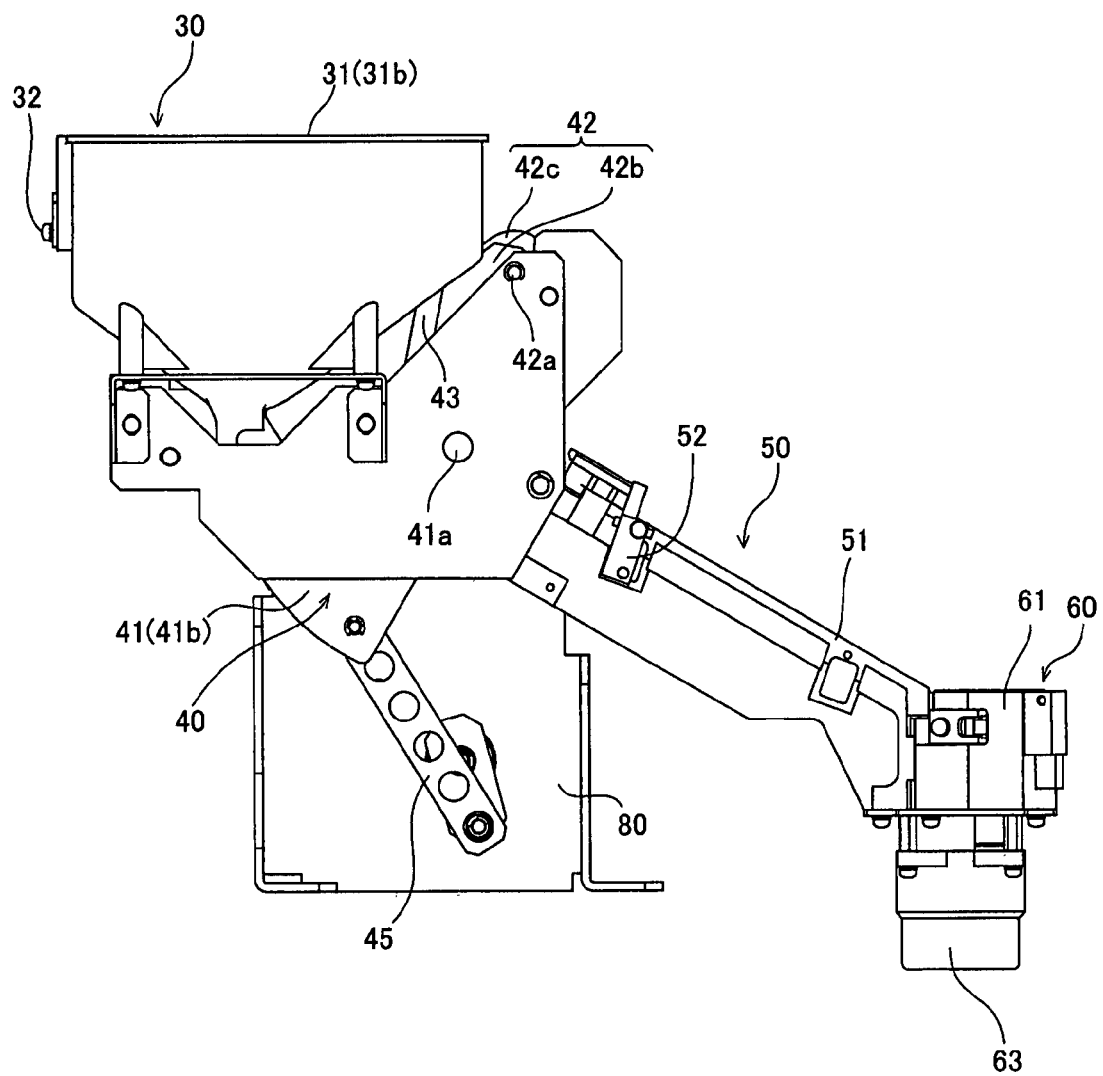
FIG. 14 is a side view of FIG. 11.

The oscillating rail 41 includes a pair of metal fan-shaped plates 41b, and a stationary resin spacer 41c sandwiched between the pair of fan-shaped plates 41b. As shown in FIG. 13, the spacing D (thickness of the spacer 41c) between the pair of fan-shaped plates 41b is smaller than the diameter D1 (refer to FIG. 5) of the flange 200a of the cuvette 200 and larger than the diameter D2 (refer to FIG. 5) of the body 200b. The oscillating guide 42 includes a pair of guide plates 42b provided to make contact with the outer side of the pair of fan-shaped plates 41b of the oscillating rail 41, and a stationary resin spacer 42c sandwiched between the pair of guide plates 42b. As shown in FIG. 16, a cuvette 200 is moved to the moving rail 51 of the moving section 50 between the oscillating rail 41 and the spacer 42c of the oscillating guide 42 in conjunction with the oscillation of the oscillating rail 41 and oscillating guide 42.

The cuvette take-out section 40 takes out the cuvettes 200 one by one via the oscillating rail 41 and the oscillating guide 42. Specifically, as shown in FIG. 15, the spacing D4 between the spacer 41c of the oscillating rail 41 and the spacer 42c of the oscillating guide 42 is set larger than the diameter D1 (refer to FIG. 5) of the flange 200a of the cuvette 200 but not so large as to allow two cuvettes 200 to enter. As shown in FIG. 13, the spacing D5 of the pair of guide plates 42b is larger than the diameter D1 (refer to FIG. 5) of the flange 200a of the cuvette 200, but not so large as to allow two cuvettes 200 to enter. Thus, only a single cuvette 200 is positioned at the take-out position 46 (refer to FIGS. 13 and 15).

As shown in FIGS. 13 and 15, the orientation of the cuvette 200 at the take-out position 46 is parallel to the oscillating rail 41 and the open end of the cuvette 200 may be either in the arrow F direction or arrow G direction. That is, when the cuvette 200 moves up the oscillating rail 41, the spacer 41c of the oscillating rail 41 ends at the position 47 midway on the fan-shaped plate 41b, as shown in FIG. 16. Thus, the closed end of the cuvette 200 drops downward under its own weight at the position 47 at which the spacer 41c ends. Since the spacing D3 (refer to FIG. 13) of the pair of fan-shaped plates 41b is less than the diameter D1 (refer to FIG. 5) of the flange 200a of the cuvette 200 but larger than the diameter D2 (refer to FIG. 5) of the body 200b as previously mentioned, the flange 200a is supported by the pair of fan-shaped plates 41b, as shown in FIG. 16. Thus, the cuvette take-out section 40 is configured such that the open end of the cuvette 200 is caused to face upward via the process of taking up the cuvette 200.

Moreover, the oscillating rail 41 and oscillating guide 42 function to agitate the cuvettes 200 stored in the second hopper 31 by being oscillated by the drive motor 44. In this way the cuvette 200 can be disposed at the take-out position 46 (refer to FIGS. 13 and 15), and interference with the take-out operation (oscillation operation by the oscillating rail 41 and oscillating guide 42) caused by a plurality of cuvettes 200 massed in a group can be avoided.

The controller 4a reverses the rotation direction of the drive motor 44 at 3 second intervals. Therefore, when oscillation of the oscillating rail 41 and oscillating guide 42 is hampered by a group of cuvettes 200, the grouping of the cuvettes 200 can be broken up by oscillating in the opposite direction. There is no change in the oscillation path of the oscillating rail 41 and oscillating guide 42 even when the drive motor 44 rotation direction is reversed.

In the present embodiment, the speed at which the cuvette 200 is moved by the cuvette transport section 20 from the first storage section 10 to the second storage section 31 is less than the speed at which the cuvette take-out section 40 takes up the cuvettes 200 from the second storage section 31 to the moving section 50. Specifically, during the time the cuvette transport section 20 moves a single cuvette 200, the cuvette take-out section 40 moves up to three cuvettes 200.

Figure 6:
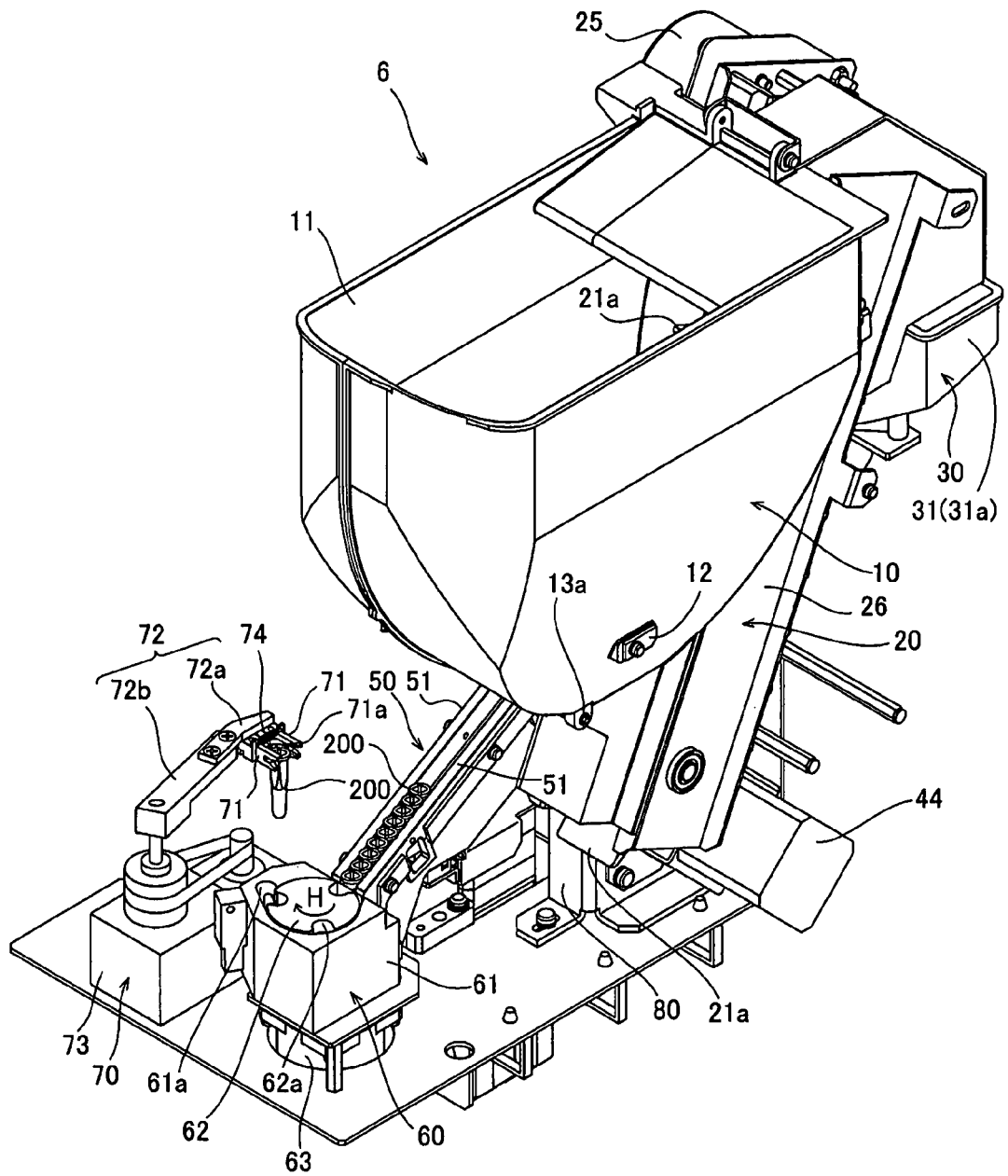
FIG. 6 is a perspective view of the cuvette feeder device of the sample analyzer shown in FIG. 2.

The moving section 50 includes a pair of moving rails 51, reflection type sensor 52, and resin buffer panel 53. The pair of moving rails 51 disposed so as to be mutually parallel with a spacing D6 (refer to FIG. 13) which is smaller than the diameter D1 of the flange 200a of the cuvette 200, and larger than the diameter D2 of the body 200b of the cuvette 200. The spacing D6 of the moving rails 51 is equal to the spacing D3 of the pair of fan-shaped plates 41b of the oscillating rail 41. Therefore, the cuvette 200 moves smoothly from the cuvette take-out section 40 to the moving rail 51. With the flange 200a engaged with the top surfaces of the pair of moving rails 51, the cuvette 200 slides downward toward the rotating part 60 which is described later. As shown in FIG. 6, the moving rails 51 is capable of accommodating a row of a predetermined amount of lined up cuvettes 200, and when the amount of cuvettes 200 accommodated on the moving rails 51 exceeds a predetermined amount, the sensor 52 detects their presence (refer to FIG. 7). In the present embodiment, when this presence is detected by the sensor 52, the controller 4a stops the moving of cuvettes from the first storage section 10 to the second storage section 30, and the take out of cuvettes from the second storage section 30 to the moving part 50 by stopping the operation of the drive motor 25 and the drive motor 44. The resin buffer plate 53 functions to reduce the energy of the cuvette 200 taken out by the cuvette take-out section 40 via the springiness of the buffer plate 53. That is, the energy of the cuvette 200 dropping under its own weight from the oscillating rail 41 at the dead center point is reduced by contacting the buffer plate 53. Therefore, for example, a problem that a taken out cuvette 200 overrides another cuvette 20 queued on the moving rail 51 is prevented (refer to FIG. 6).

Figure 7:
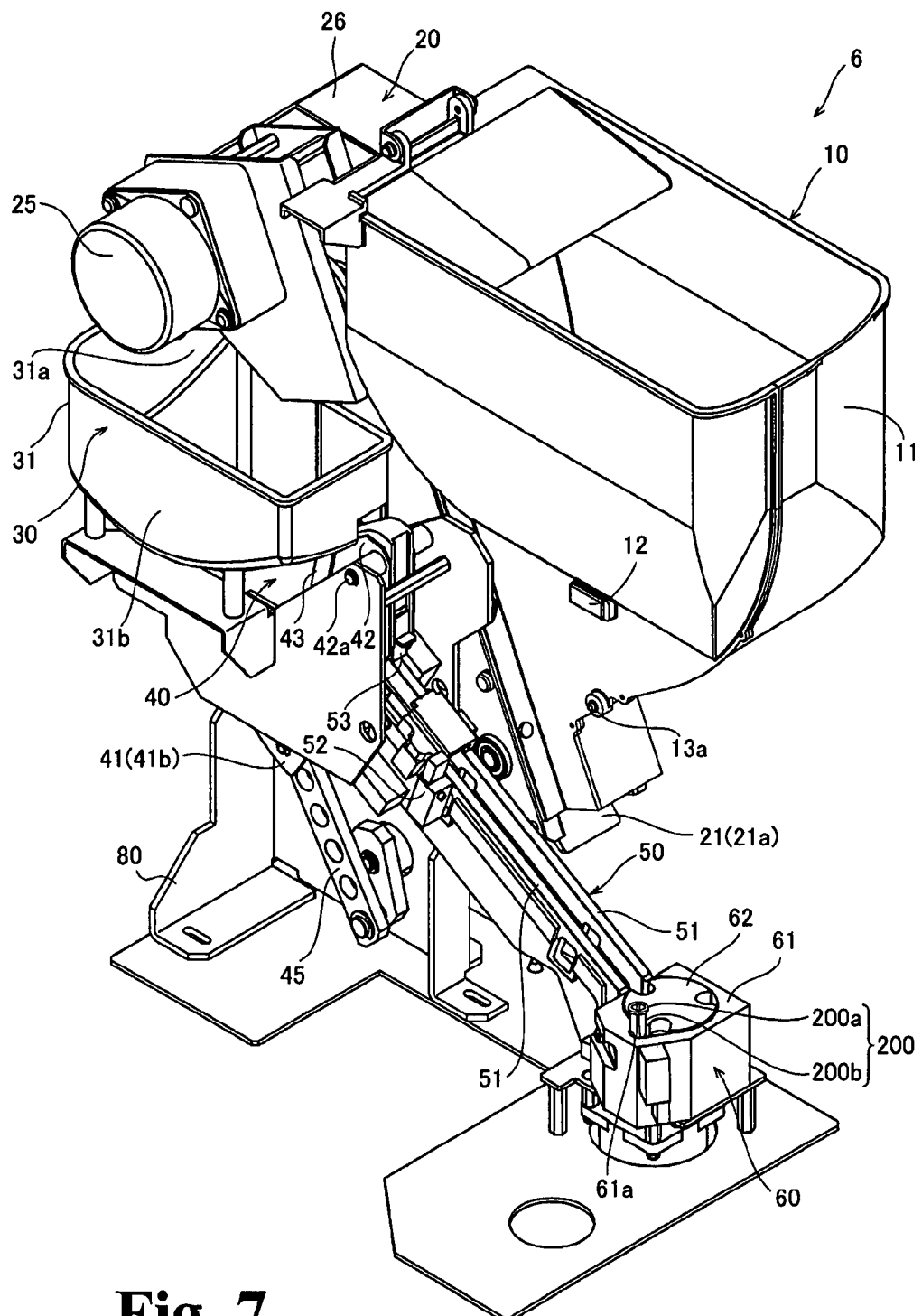
FIG. 7 is a perspective view showing the cuvette feeder shown in FIG. 6 with the catcher section removed.
Figure 8:
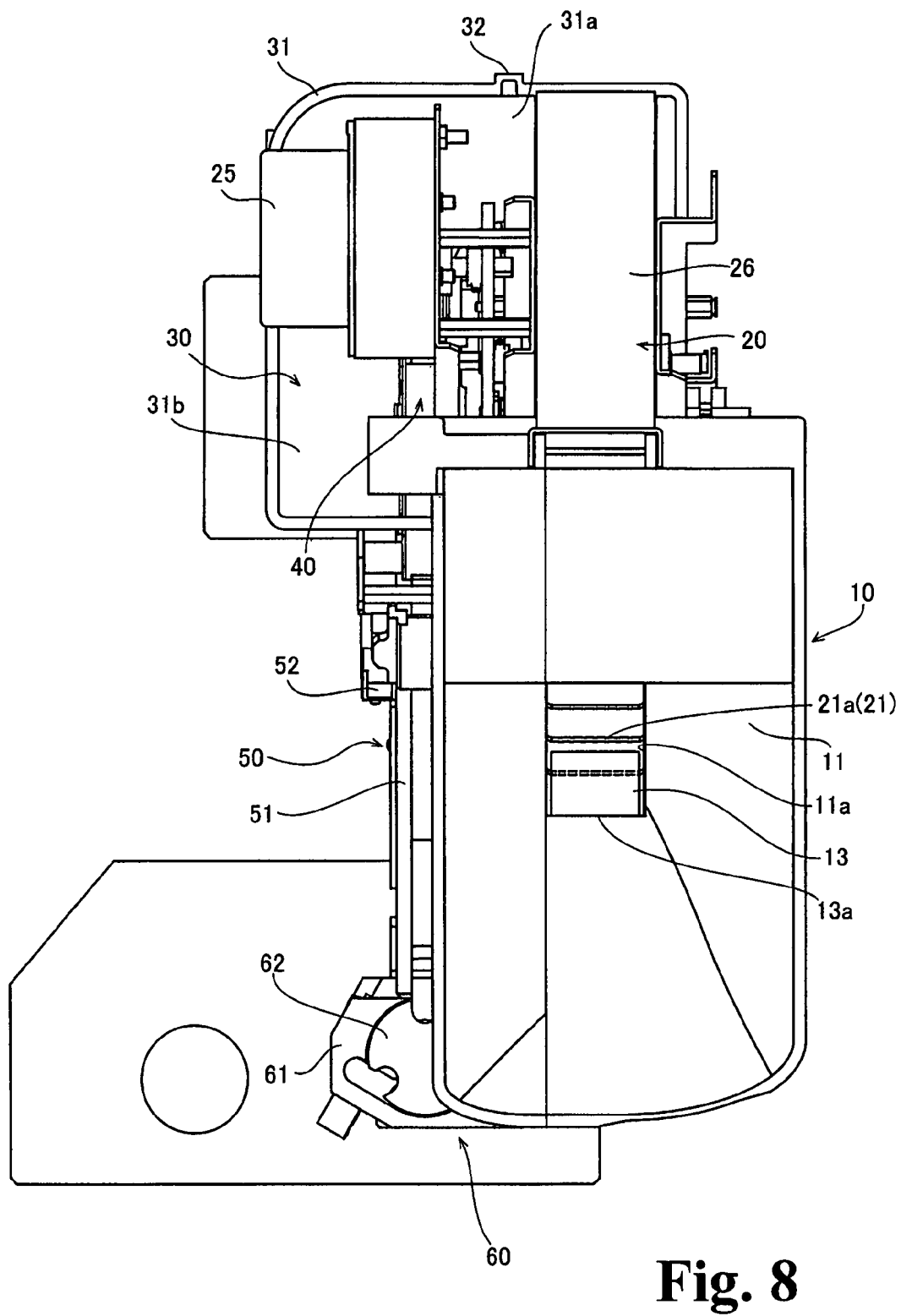
FIG. 8 is a top view of FIG. 6.

The rotating part 60 functions to rotate the cuvette 200, which has slid down the moving rail 51, in the arrow H direction to the waiting position at which it can be grasped by the catcher 70. The rotating part 60 includes a support platform 61, rotating table 62 which is mounted on the support platform 61 so as to be rotatable, and drive motor 63 for driving the rotating table 62. The rotating table 62 is rotated in the arrow H direction by the drive motor 63 to move the cuvettes 200 inserted in the three notches 62a of the of the rotating table 62 to the notch 61*a* (waiting position) of the support platform 61. Although not shown in the drawings, the bottom surface where the rotating table 62 is inserted in the support platform 61 is an inclined surface that gradually becomes higher along the moving path of the cuvette 200 on the rotating table 62. Therefore, when the cuvette 200 is moved by the rotating table 62 and reaches the notch 61*a* of the support platform 61 disposed at the waiting position, the flange 200*a* of the cuvette 200 protrudes from the top surface of the rotating table 62, as shown in FIG. 7. The catcher 70 can therefore grasp the flange 200*a* of the cuvette 200.

Figure 17:
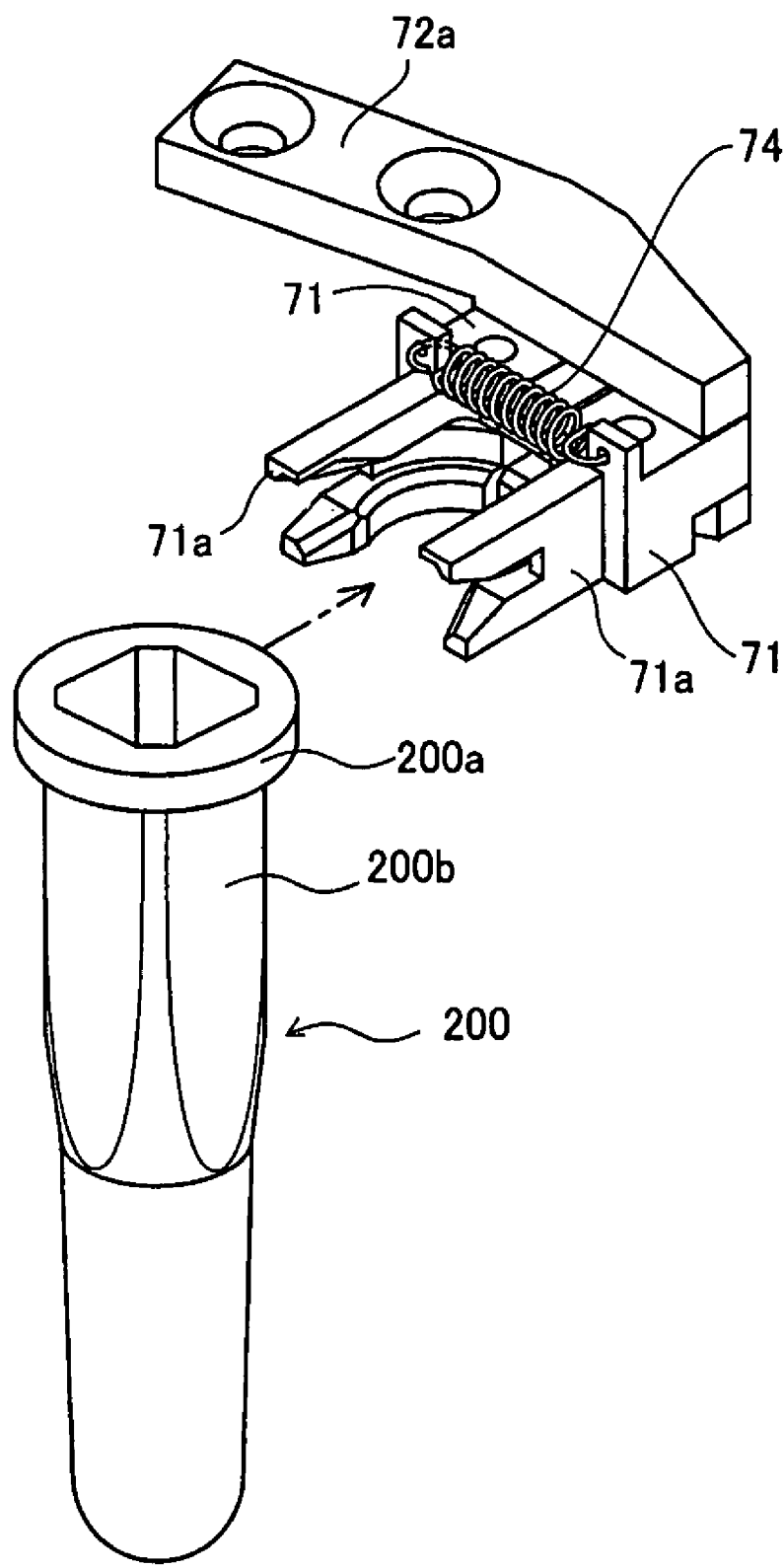
FIG. 17 is a perspective view of the grip of the catcher of the cuvette feeder device of FIG. 6 and the cuvette.
Figure 18:
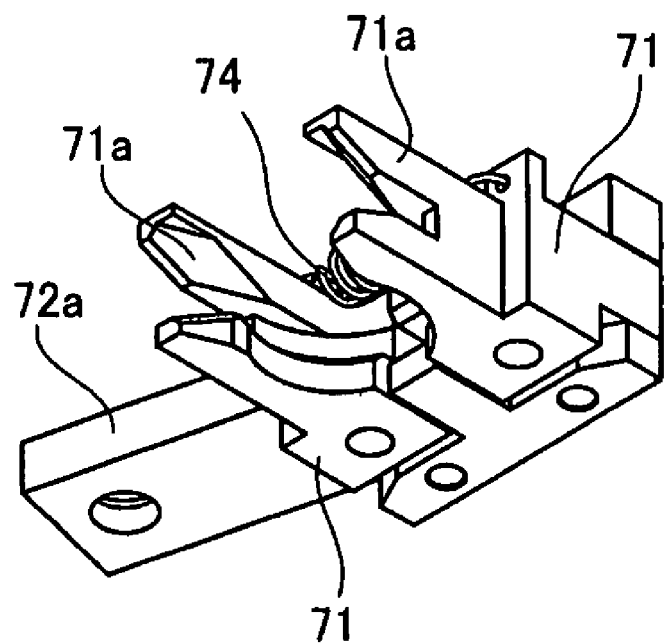
FIG. 18 is a perspective view of the grip of the catcher of the cuvette feeder device of FIG. 6.

The catcher 70 is provided to supply a cuvette 200, which has been moved to the notch 61*a* at the waiting position of the support platform 61 via the rotating part 60, to the dispensing table 103 (refer to FIG. 3) of the rotating part 100 of the analyzing section 7. As shown in FIGS. 6, 17, and 18, the catcher 70 includes a pair of gripping members 71 for gripping a cuvette 200, first arm 72*a* on which are mounted the gripping members 71, second arm 72*b* on which is mounted the first arm 72*a*, and drive section 73 (refer to FIG. 6) for driving the arm section 72 configured by the first arm 72*a* and second arm 72*b*. The pair of gripping members 71 have two-pronged grips 71*a*, and a compression spring 74 that exerts a force to mutually draw the grips 71*a* closer together. The cuvette 200 is grasped by the grip members 71 when the pair of grip members 71 widen against the force exerted by the compression spring 74 and the flange 200*a* of the cuvette 200 is gripped between the two-pronged grips 71*a*. The drive section 73 rotates the arm 72 in horizontal directions, and moves the arm 72 in vertical directions.

As shown in FIGS. 2 and 3, the analyzing section 7 is provided with a rotating part 100, sample dispensing arm 110, first optical information acquiring section 120, lamp unit 130, reagent dispensing arm 140, cuvette moving section 150, second optical information acquiring section 160, urgent sample placement section 170, fluid flow section 180.

The rotating part 100 is provided to move in a rotational direction the cuvette 200 supplied from the cuvette feeder 6, and reagent container (not shown in the drawing) containing reagent to be added to the sample in the cuvette 200. As shown in FIG. 3, the rotating part 100 is configured by a circular reagent table 101, annular reagent table 102 disposed on the outer side of the circular reagent table 101, and annular dispensing table 103 disposed on the outer side of the annular reagent table 102. The dispensing table 103, reagent table 101 and reagent table 102 are capable of rotating in both clockwise and counterclockwise directions, and each table rotates in mutual independence from the others.

The reagent tables 101 and 102 respectively include a plurality of holes 101*a* and 102*a* provided at predetermined intervals in the circumferential direction, as shown in FIG. 3. The holes 101*a* and 102*a* of the reagent tables 101 and 102 are provided for holding a plurality of reagent containers (not shown in the drawing) which contain various reagents to be added when preparing a measurement sample from a sample. Furthermore, the dispensing table 103 includes a plurality of cylindrical holders 103*a* provided at predetermined spacing in the circumferential direction. The holder 103*a* is provided to hold the cuvettes 200 received from the cuvette feeder 6. A sample contained in a test tube 250 of the moving section 3 is dispensed to a cuvette 200 held by the holder 103*a* of the dispensing table 103 in the dispensing process.

The sample dispensing arm 110 functions to both aspirate sample contained in a test tube 250 transported to the aspiration position 2*a* via the moving section 3, and to dispense the aspirated sample into a cuvette 200 transported to the rotating part 100.

The first optical information acquiring section 120 is configured so as to acquire optical information from a sample in order to measure the presence and concentration of interference substances (hemoglobin, bilirubin, chyle) in the sample before adding reagent. Specifically, the presence and concentrations of interference substances are measured using four types of light (405 nm, 575 nm, 660 nm, 800 nm) among five types of light (340 nm, 405 nm, 575 nm, 660 nm, 800 nm) emitted from the lamp unit 130 described later. The 405 nm wavelength light is absorbed by chyle, hemoglobin, and bilirubin. That is, chyle, hemoglobin, and bilirubin influence the optical information measured using light at a wavelength of 405 nm. Furthermore, light at a wavelength of 575 nm is absorbed by chyle and hemoglobin, although essentially is not absorbed by bilirubin. That is, chyle and hemoglobin influence the optical information measured using light at a wavelength of 575 nm. Light at wavelengths of 660 nm and 800 nm are absorbed by chyle, although essentially are not absorbed by bilirubin and hemoglobin. That is, chyle influences the optical information measured using light at wavelengths of 660 nm and 800 nm. Chyle absorbs light from the low wavelength region 405 nm to the high wavelength region 800 nm, with chyle absorbing more light at the 660 nm wavelength than at the 800 nm wavelength. That is, the optical information measured using light at the 800 nm wavelength is less influenced by chyle than optical information at the 660 nm wavelength.

The acquisition of sample optical information by the first optical information acquiring section 120 occurs before optically measuring (main measurement) the sample by the second optical information acquiring section 160. The first optical information acquiring section 120 acquires optical information from the sample within the cuvette 200 held by the holder 103*a* of the dispensing table 103.

The first optical information acquiring section 120 is electrically connected to the controller 4*a* of the control device 4, and sends data (optical information) acquired by the first optical information acquiring section 120 to the controller 4*a* of the control device 4. Thus, in the control device 4 the light absorbance of the sample within the cuvette 200 is determined relative to the five kinds of light emitted from the beam splitter optical fiber 131, and the presence and concentrations of interference substances in the sample are analyzed by performing data analysis of the data from the first optical information acquiring section 120. In the present embodiment, a determination is made as to whether or not to analyze optical information acquired by the second optical information acquiring section 160 based on the presence and concentrations of interference substances in the sample.

The lamp unit 130 is provided to supply light of five wavelengths (340 nm, 405 nm, 575 nm, 660 nm, 800 nm) to be used for the optical measurements performed by the first optical information acquiring section 120 and the second optical information acquiring section 160, as shown in FIG. 3. That is, a single lamp unit 130 is configured so as to be used jointly by the first optical information acquiring section 120 and second optical information acquiring section 160. The light of the lamp unit 130 is supplied to the first optical information acquiring section 120 and the second optical information acquiring section 160 by the beam splitter optical fiber 131 and beam splitter optical fiber 132, respectively.

As shown in FIGS. 2 and 3, the reagent dispensing arm 140 is provided to mix reagent with the sample in the cuvette 200 by dispensing the reagent within a reagent container (not shown in the drawings) loaded on the rotating part 100 into a cuvette 200 held in the rotating part 100. In this way a measurement sample is prepared by adding reagent to a sample after the sample has been optically measured by the first optical information acquiring section 120. The cuvette moving section 150 is provided to move the cuvette 200 between the rotating part 100 and the second optical information acquiring section 160.

The second optical information acquiring section 160 functions to heat the measurement sample prepared by adding reagent to a sample, and measure optical information from the measurement sample. As shown in FIG. 3, the second optical measurement section 160 is configured by a cuvette loader 161, and detection unit 162 disposed below the cuvette loader 161. The cuvette loader 161 has a built-in heater (not shown in the drawing) for heating a cuvette 200 to a predetermined temperature.

The detection unit 162 of the second optical information acquiring section 160 is provided to make possible the optical measurement (main measurement) of a measurement sample within a cuvette 200 under a plurality of conditions. The second optical information acquiring section 160 is electrically connected to the controller 4a of the control device 4, and sends acquired data (optical information) to the controller 4a of the control device 4. Thus, the data (optical information) received from the second optical information acquiring section 160 is analyzed in the control device 4 based on the analysis result of the data (optical information) previously acquired by the first optical information acquiring section 120, and the analysis results are displayed on the display 4b.

The 660 nm wavelength light emitted from the beam splitter optical fiber 132 is used as the main wavelength when measuring Fbg (fibrinogen content), PT (prothrombin time), and APTT (active partial thromboplastin time). The 800 nm wavelength light is a sub wavelength used when measuring Fbg, PT, and APTT. The 405 nm wavelength is used for measuring ATIII, which is a measurement item in the synthetic substrate method, and 800 nm wavelength light is used to measure D dimer and FDP, which are measurement items in the immunoturbidity method. The wavelength for measuring platelet coagulation is 575 nm.

The urgent sample placement section 170 is provided for the processing of an urgent sample for samples requiring urgent attention, as shown in FIGS. 2 and 3. The urgent sample placement section 170 is configured so as to allow an urgent sample to interrupt an on-going sample analysis process of a sample supplied from the moving section 3. The fluid flow section 180 is provided to supply a fluid such as cleaning fluid to nozzles provided in each dispensing arm (sample dispensing arm 110 and reagent dispensing arm 140) during the shutdown process of the sample analyzer 1.

The analyzing section 7 is provided with disposal hole 181 (refer to FIG. 3) provided at predetermined spacing from the previously mentioned catcher 70, and a disposal box 182 disposed below the disposal hole 181, as shown in FIGS. 2 and 3. The catcher 70 disposes of the cuvette 200 of the rotating part 100 in the disposal box 182 through the disposal hole 181 (refer to FIG. 3). That is, the catcher 70 both supplies and disposes of the cuvettes 200.

The cuvette feeding operation performed by the cuvette feeder 6 of the present embodiment of the sample analyzer 1 is described below with reference to FIGS. 1, 6, 9, 13, 15, and 16.

The user first supplies a cuvette 200 in the first hopper 11. Thereafter, the cuvette 200 feeding operation starts when the measurement start button 5c (refer to FIG. 1) is pressed or the measurement start operation is performed by the control device 4. That is, the drive motor 25 of the cuvette transport section 20, drive motor 44 of the cuvette take-out section 40, drive motor 63 of the rotating part 60, and drive motor 73 of the catcher 70 are actuated.

As shown in FIG. 9, the cuvettes 200 stored in the first hopper 11 are held by the holding panel 21a of the endless belt 21 and moved upward from the bottom part of the first hopper 11 via the drive force of the drive motor 25. During cuvette transportation, the amount and orientation of the cuvettes 200 held by the holding part 21a are irregular. When the endless belt 21 is further rotated, the cuvettes 200 are dropped to the cuvette receiver 31a of the second hopper 31 positioned on the opposite side of the endless belt 21 from the first hopper 11.

The cuvettes 200 that fall to the cuvette receiver 31a are automatically moved to the cuvette stacker 31b via the inclination of the bottom surface of the cuvette receiver 31a. As shown in FIGS. 13, 15, and 16, the cuvettes 200 in the cuvette stacker 31b are agitated by the oscillating rail 41 and oscillating guide 42 of the cuvette take-out section 40 as they are taken out and move one by one to the moving rail 51 of the moving part 50. When the cuvettes 200 are taken out one by one, the oscillating rail 41 manages the orientation of the cuvette 200 such that the closed end faces downward. In the present embodiment, the amount of cuvettes 200 stored in the second hopper 31 is approximately two to ten cuvettes. Therefore, the cuvettes take-out section 40 can take out cuvettes 200 one by one at a stable speed compared to when many cuvettes 200 are stored in the second hopper 31. No more than the necessary amount of cuvettes 200 are stored in the second hopper 31 since the speed at which the cuvette take-out section 40 takes out the cuvettes 200 is set so as to be slower than the speed at which cuvettes 200 are transported by the cuvette transport section 20.

The cuvette 200 is moved toward the support platform 61 while sliding down along the moving rails 51 under its own weight with the flange 200a engaged with the top surface of the pair of moving rails 51. The catcher 70 stops supplying the cuvettes 200, depending on the processing conditions of the analyzing section 7. Therefore, the cuvettes 200 wait on the moving rails 51, as shown in FIG. 6. When a predetermined amount of cuvettes 200 wait on the moving rails 51, the sensor 52 detects the cuvettes 200. In this case, the controller 4a stops the operation of the cuvette take-out section 40 and cuvette transport section 20.

The cuvette 200 that reaches the bottom end of the moving rail 51 is moved by the rotating part 60 disposed at the bottom end of the moving rails 51 to the notch 61a (refer to FIG. 13) of the support platform 61 at the waiting position at which the cuvette can be grasped by the catcher 70. Then, flange 200a of the cuvette 200 is grasped between the grip members 71 of the catcher 70 and moved to the dispensing table 103 of the rotating part 100 of the analyzing section 7, as shown in FIG. 6.

The cuvette 200 is supplied in this manner in the present embodiment of the sample analyzer 1.

The sample analysis operation performed by the sample analyzer 1 is described below with reference to FIGS. 2 and 3. The operation of performing measurements using the coagulation time method is described below.

The sample analyzer 1 is initialized by switching ON the respective power sources of the detection section 2 and control device 4 of the sample analyzer 1 shown in FIG. 2. Thus, an operation is performed to return the devices for moving the cuvettes 200 and each dispensing arm (sample dispensing arm 110 and reagent dispensing arm 140) to their initial positions, and the software store din the controller 4a of the control device 4 is initialized.

Then, the moving section 3 shown in FIG. 3 moves the rack 251 loaded with test tubes 250 containing samples. In this way the rack 251 at the rack placement region 3a is moved to a position corresponding to the aspirating position 2a of the detection section 2.

Next, a predetermined amount of the sample is aspirated from the test tube 250 by the sample dispensing arm 110. Then, the sample dispensing arm 110 is moved above the cuvette 200 held on the dispensing table 103 of the rotating part 100. Thereafter, part of the sample is allocated into the cuvette 200 by discharging sample from the dispensing arm 110 into the cuvette 200 on the dispensing table 103.

The dispensing table 103 is then rotated, and the cuvette 200 to which the sample was dispensed is moved to a position at which measurements can be performed by the first optical information acquiring section 120. In this way optical information is obtained from the sample by the first optical information acquiring section 120 optically measuring the sample. Specifically, data, which is composed of electrical signals derived from the five types of light (340 nm, 405 nm, 575 nm, 660 nm, 800 nm) transmitted through the sample within the cuvette 200 held by the holder 103a of the dispensing table 103, are sent to the controller 4a of the control device 4. Thus, the acquisition of optical information (first optical information) from the sample by the first optical information acquiring section 120 is completed.

The controller 4a of the control device 4 calculates the light absorption of the sample using the received data (first optical information), calculates the light absorption of the sample using the interference substances (chyle, hemoglobin, bilirubin) in the sample, and calculates the presence and concentrations of the interference substances (chyle, hemoglobin, bilirubin) in the sample. Specifically, the controller 4a of the control device 4 calculates the light absorption of the sample based on the optical information (first optical information) obtained using four types of light (405 nm, 575 nm, 660 nm, 800 nm) emitted from the lamp unit 130, and stores the light absorption in the RAM 401c.

Thereafter, a determination is made as to whether or not the light absorption at the main wavelength is below a threshold value among the light absorptions stored in the RAM 401c. Specifically, when the sample measurement item is an item using the coagulation time method such as PT, APTT, Fbg or the like, a determination is made as to whether or not the light absorbance calculated from the first optical information measured using light of the main 660 nm wavelength is less than a threshold value (for example, 2.0).

When the light absorption at the main wavelength calculated from the first optical information measured by the first optical information acquiring section 120 is less than the threshold value, the reagent dispensing arm 140 is actuated and the reagents within the reagent containers loaded in the reagent tables 101 and 102 are added to the sample within the cuvette 200 on the dispensing table 103. Thus, a measurement sample is prepared. Then, the cuvette 200 containing the measurement sample on the dispensing table 103 is moved to the cuvette loader 161 of the second optical information acquiring section 160 using the cuvette moving section 150.

The detection unit 162 of the second optical information acquiring section 160 acquires optical information (second optical information) from the sample by optically measuring the measurement sample in the cuvette 200 under a plurality of conditions via the detection section 162 of the second optical information acquiring section 160. Specifically, the cuvette 200 disposed in the cuvette loader 161 is first heated to a predetermined temperature by a heating device (not shown in the drawing). Thereafter, light emitted from the bema splitter optical fiber of the lamp unit 130 illuminates the cuvette 200 on the cuvette loader 161. Five different wavelength of light (340 nm, 405 nm, 575 nm, 660 nm, 800 nm) are emitted from the beam splitter optical fiber 132. Electrical signal data corresponding to the light emitted form the beam splitter optical fiber 132 of each wavelength transmitted through the cuvette 200 and the measurement sample within the cuvette 200 is acquired.

The electrical signal data corresponding to the light of the five different wavelengths are sequentially sent to the controller 4a of the control device 4. Thus, the acquisition of optical information (second optical information) from the sample by the second optical information acquiring section 160 is completed.

When the light absorption at the main wavelength calculated from the first optical information measured by the first optical information acquiring section 120 is greater than the threshold value, a determination is made as to whether or not the light absorption at the sub wavelength calculated from the first optical information measured by the first optical information acquiring section 120 is less than the threshold value. Specifically, when the sample measurement item is an item using the coagulation time method such as PT, APTT, Fbg or the like, a determination is made as to whether or not the light absorbance calculated from the first optical information measured using light of the main 800 nm wavelength is less than a threshold value (for example, 2.0).

When the light absorption at the sub wavelength calculated from the first optical information measured by the first optical information acquiring section 120 is less than the threshold value, optical information (second optical information) is acquired by measuring the measurement sample via the second optical information acquiring section 160.

However, when the light absorption at the sub wavelength calculated from the first optical information measured by the first optical information acquiring section 120 is greater than the threshold value, highly reliable analysis is deemed difficult due to the overwhelming influence of the interference substances (chyle, hemoglobin, bilirubin) in the sample, and, therefore, the main measurement is terminated. Thus, wasteful use of reagent is prevented since a measurement sample is not prepared by adding reagent to a sample that can not be analyzed due to the excessive influence of interference substances. Instances of when it is difficult to make highly reliable measurements (when the main measurement is terminated), include cases in which the transmission light passing through the sample can not be materially detected because the light is blocked due to the presence of large amounts of interference substances in the sample detected by the first optical information acquiring section 120.

After the acquisition of the second optical information (main measurement) by the second optical information acquiring section 160, the second optical information of the sample measured at the sub wavelength is sent to the controller 4a of the control device 4 among the plurality of second optical information measured by the second optical information acquiring section 160, and analyzed by the application program 404a installed on the hard disk 401d of the controller 4a. For example, when the sample measurement item is PT, the second optical information measured using the light of the main wavelength 660 nm is sent to the controller 4a of the control device 4. Thereafter, the controller 4a, which has received the second optical information acquired at the main wavelength, outputs the analysis result based on this second optical information.

Similarly, after the acquisition of the second optical information (main measurement) by the second optical information acquiring section 160, the second optical information of the sample measured at the sub wavelength is sent to the controller 4a of the control device 4 among the plurality of second optical information measured by the second optical information acquiring section 160, and analyzed by the application program 404a installed on the hard disk 401d of the controller 4a. For example, when the sample measurement item is PT, the second optical information measured using the light of the main wavelength 800 nm is sent to the controller 4a of the control device 4. Thereafter, the controller 4a, which has received the second optical information acquired at the sub wavelength, outputs the analysis result based on this second optical information.

After the analysis is completed by the controller 4a of the control device 4, the obtained analysis results are displayed on the display 4b of the control device 4. Thus, the sample analysis operation is completed by the sample analyzer 1.

By providing a first storage section 10 for storing a plurality of cuvettes 200 for preparing samples, a cuvette transport section 20 for moving a plurality of cuvettes 200 from the first storage section 10, and a second storage section 30 for storing a plurality of cuvettes 200 moved by the cuvette transport section 20 in the present embodiment, a small portion of cuvettes 200 are stored in the second storage section 30 even when a large amount of cuvettes 200 are stored in the first storage section 10. For this reason, jamming of the cuvettes 200 in the second storage section 30 caused by the pressure of a large amount of cuvettes 200 at the top pressing on the cuvettes 200 at the bottom is avoided. Therefore, cuvettes 200 can be stably fed. By providing a moving rail 51 to move cuvettes 200 one by one from the second storage section 30, and adjusting the amount of cuvettes 200 transported by the cuvette transport section 20 to the second storage section 30 based on the detection result of the sensor 52 that detects the state of transporting cuvettes 200 by the moving rail 51, the amount of cuvettes 200 stored in the storage section 30 can be controlled so as to not increase when moving of cuvettes 200 by the moving rail 51 is unnecessary. In this case, the cuvettes 200 are fed with more stability since jamming of the cuvettes 200 is prevented in the second storage section 30. By configuring the cuvette transport section 20 to move a plurality of cuvettes 200 from the first storage section 10, and configuring the moving rail 51 to move the cuvettes 200 from the second storage section 30 one by one, it is not necessary to move a large quantity of cuvettes 200 one by one from the first storage section 10 to the second storage section 30. Therefore, cuvettes 200 can be moved smoothly from the large capacity first storage section 10 to the second storage section 30. This also allows cuvettes 200 to be fed with greater stability.

In the present embodiment, the moving rails 51 move a plurality of cuvettes 200 and align them in a row, and the sensor 52 detects whether the amount of cuvettes 200 aligned on the moving rails 51 exceeds a predetermined value, such that the operation of the endless belt 21 can be stopped when the controller 4a detects via the sensor 52 that the amount of cuvettes 200 aligned on the moving rails 51 exceeds a predetermined value. In this way when the amount of cuvettes 200 aligned on the moving rails 51 exceeds a predetermined amount, the movement of the cuvettes 200 from the first hopper 10 to the second hopper 31 by the endless belt 21 can be stopped. Therefore, storing an unnecessary excess amount of cuvettes 200 in the second storage hopper 31 can be readily prevented.

In the present embodiment, cuvettes 200 being stored in the first storage section 10 are easily transported, and the cuvettes 200 is easily prevented from being left at the bottom of the first storage section 10 by having the drive motor 25 rotate the endless belt 21 which is provided with a plurality of holding panels 21a capable of holding the cuvettes 200.

In the present embodiment, cuvettes 200 can be prevented from falling through the opening 11a at the bottom of the first hopper 10 and jamming of at the opening 11a by providing the movable plate 13 to cover the opening 11a of the first hopper 11.

In the present embodiment, cuvettes 200 are easily fed one by one from the second hopper 31 to the moving rail 51 by the cuvette take-out section 40.

In the present embodiment, the orientation of the cuvette 200 can changed to an orientation suited for being supplied by the cuvette take-out section 40 by the cuvette take-out section 40 agitating the cuvette 200 stored in the second hopper 31.

In the present embodiment, an increase in the amount of cuvettes 200 stored in the second hopper 31 can be prevented by setting the speed of the movement of the cuvette transport section 10 so as to be less than the speed of the movement of the cuvette take-out section 40.

In the present embodiment, jamming of cuvettes 200 in the second hopper 31 can be prevented by setting the storage capacity of the second hopper 31 so as to be less than the storage capacity of the first hopper 11.

In the present embodiment, an overflow of cuvettes 200 from the second hopper 31 is prevented because storage of cuvettes 200 in the second hopper 31 in excess of a predetermined amount is prevented by the sensor 32.

The embodiment disclosed herein is to be considered an example in all aspects and in no way limiting. The scope of the present invention is defined by the scope of the claims and not by the description of the embodiment, and includes all modifications within the scope of the claims and the meanings and equivalences therein.

Figure 19:
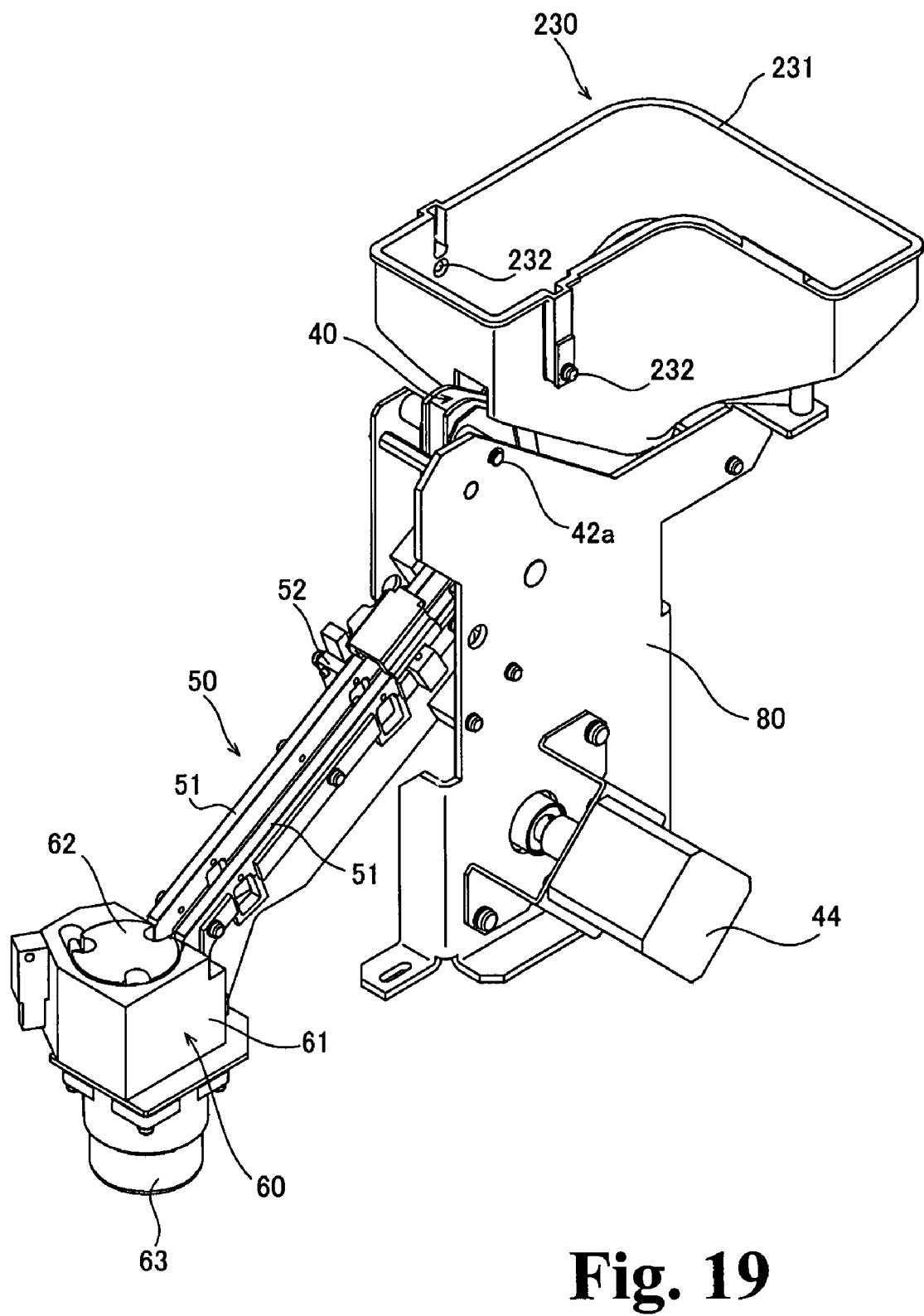
FIG. 19 is a perspective view of the second storage section in a variation of the embodiment of the sample analyzer of the present invention.

For example, although the operation of the cuvette take-out section 40 and cuvette transport section 20 (refer to FIG. 9) are stopped based on the detection of the sensor 52 of the moving section 50 in the present embodiment, the present invention is not limited to this arrangement inasmuch as a transmission type sensor 232 may be provided to detect the storage of cuvettes 200 in a second hopper 231 in excess of a predetermined amount, so as to stop the operation of the cuvette take-out section 40 based on the detection of the sensor 52 of the moving section 50, and stop the operation of the cuvette transport section 20 (refer to FIG. 9) based on the detection of the sensor 232, as in the case of the second storage section 230 of the modification shown in FIG. 19. In this configuration, too, storing an unnecessary excess amount of cuvettes 200 in the second storage hopper 31 can be readily prevented.

Although the cuvette transport section 20 is provided as a transporting means for transporting cuvettes 200 from the first storage section 10 to the second storage section 30 in the example of the present embodiment, the present invention is not limited to this arrangement inasmuch as a transporting means independent of the cuvette transport section 20 also may be provided.

Although the moving section 50 is provided with the sensor 52 which can detect the amount of containers taken out by the cuvette take-out section 40 from the second storage section 30, the present invention is not limited to this arrangement inasmuch as a sensor which can detect the amount of containers taken out by the cuvette take-out section 40 from the second storage section 30 may be provided in the second hopper 31, the cuvette take-out section 40 and the like.

What is claimed is:

1. A sample analyzer comprising:
a first hopper for storing a plurality of containers, the containers used for preparing a measurement sample;
a transport section for transporting the containers stored in the first hopper;
a second hopper for storing the containers transported by the transport section;
a container take out section including means for taking out one by one the containers stored in the second hopper to a moving section;
the moving section including means for arranging the containers taken out by the container take out section in a row;
a detector for detecting whether an amount of containers arranged by the moving section exceeds a predetermined value;
a controller in communication with the transport section configured to control an operation of the transport section based on a detection result of the detector;
a sample preparing section for preparing a measurement sample in a container supplied by the moving section; and
an analyzing section for analyzing the measurement sample prepared by the sample preparing section.

2. The sample analyzer of claim 1,
wherein the controller stops the operation of the transport section when the detector detects that the amount of containers arranged by the moving section exceeds the predetermined value.

3. The sample analyzer of claim 1,
wherein the controller further is in communication with the container take out section and is configured to control an operation of the container take out section based on the detection result of the detector, and
wherein the controller stops the operation of the container take out section when the detector detects that the amount of containers arranged by the moving section exceeds the predetermined value.

4. The sample analyzer of claim 1,
wherein the transport section comprises an endless belt comprising a plurality of holding panels which are capable of holding containers, and a rotation device for rotating the endless belt,
wherein the holding panels move upward from the bottom of the first hopper by rotating the endless belt by the rotation device.

5. The sample analyzer of claim 4,
wherein the first hopper has an opening at the bottom, through which the holding panels pass, and
wherein the first hopper comprises a movable panel for covering the opening, which is capable of moving by contacting the holding panels.

6. The sample analyzer of claim 1, wherein
the container take out section is configured to agitate the containers stored in the second hopper within the second hopper.

7. The sample analyzer of claim 1, wherein
a transporting speed by the transport section is slower than that by the container take out section.

8. The sample analyzer of claim 1, wherein
a storage capacity of the second hopper is less than that of the first hopper.

9. The sample analyzer of claim 1, further comprising,
a second detector for detecting whether an amount of containers stored in the second hopper exceeds a second predetermined value,
wherein the controller controls the operation of the transport section based on a detection result of the second detector.

10. A sample analyzer comprising:
a first storage section for storing a plurality of containers, the containers used for preparing a measurement sample;
a transport section for transporting the containers stored in the first storage section;
a second storage section for storing the containers transported by the first transport section;
a take out section including means for taking out one by one the containers stored in the second storage section to a moving section;
the moving section including means for arranging the containers taken out by the container take out section in a row;
a first detector for detecting whether an amount of containers arranged by the moving section exceeds a first predetermined value;
a controller in communication with the transport section configured to control an operation of the transport section based on a detection result of the first detector;
a sample preparing section for preparing a measurement sample in a container supplied by the moving section; and
an analyzing section for analyzing the measurement sample prepared by the sample preparing section,
wherein the sample analyzer further comprises a second detector for detecting whether an amount of containers stored in the second storage section exceeds a second predetermined value, and
wherein the controller further controls the operation of the transport section based on a detection result of the second detector and stops the operation of the transport section when the second detector detects that the amount of containers stored in the second storage section exceeds the second predetermined value.

11. A sample analyzer comprising:
a first hopper for storing a plurality of containers, the containers used for preparing a measurement sample;
a transport section for transporting the containers stored in the first hopper;
a second hopper for storing the containers transported by the transport section;
a container take out section including means for taking out one by one the containers stored in the second hopper to a moving section;
the moving section including means for arranging the containers taken out by the container take out section in a row;
a detector for detecting whether an amount of containers arranged by the moving section exceeds a predetermined value;
a controller in communication with the container take out section configured to control an operation of the container take out section based on a detection result of the detector;
a sample preparing section for preparing a measurement sample in a container supplied by the moving section; and
an analyzing section for analyzing the measurement sample prepared by the sample preparing section.

12. The sample analyzer of claim 11,
wherein the controller stops the operation of the container take out section when the detector detects that the amount of containers arranged by the moving section exceeds the predetermined value.

13. The sample analyzer of claim 11,
wherein the controller further is in communication with the transport section and is configured to control an operation of the transport section based on the detection result of the detector, and
wherein the controller stops the operation of the transport section when the detector detects that the amount of containers arranged by the moving section exceeds the predetermined value.

14. The sample analyzer of claim 11, wherein
the container take out section is configured to agitate the containers stored in the second hopper within the second hopper.

15. The sample analyzer of claim 11, wherein
a transporting speed by the transport section is slower than that by the container take out section.

16. The sample analyzer of claim 11, wherein
a storage capacity of the second hopper is less than that of the first hopper.

17. The sample analyzer of claim 11, further comprising,
a second detector for detecting whether an amount of containers stored in the second hopper exceeds a second predetermined value,
wherein the controller further is in communication with the transport section and is configured to control an operation of the transport section based on the detection result of the second detector.

18. The sample analyzer of claim 17,
wherein the controller stops the operation of the transport section when the second detector detects that the amount of containers stored in the second hopper exceeds the second predetermined value.

* * * * *